(12) United States Patent
McShane et al.

(10) Patent No.: US 7,850,979 B2
(45) Date of Patent: Dec. 14, 2010

(54) COMPOSITIONS FOR IMMUNIZING AGAINST MYCOBACTERIUM

(75) Inventors: Helen McShane, Oxford (GB); Ansar A. Pathan, Oxford (GB); Adrian Hill, Oxford (GB); Sarah C. Gilbert, Oxford (GB)

(73) Assignee: Isis Innovation Limited, Oxford (GB)

( * ) Notice: Subject to any disclaimer, the term of this patent is extended or adjusted under 35 U.S.C. 154(b) by 371 days.

(21) Appl. No.: 11/813,397

(22) PCT Filed: Jan. 5, 2006

(86) PCT No.: PCT/GB2006/000023

§ 371 (c)(1),
(2), (4) Date: Jul. 5, 2007

(87) PCT Pub. No.: WO2006/072787

PCT Pub. Date: Jul. 13, 2006

(65) Prior Publication Data

US 2008/0226678 A1 Sep. 18, 2008

Related U.S. Application Data

(60) Provisional application No. 60/649,804, filed on Feb. 3, 2005.

(30) Foreign Application Priority Data

Jan. 5, 2005 (GB) ................................ 0500102.9

(51) Int. Cl.
*A61L 39/04* (2006.01)
*A61K 39/02* (2006.01)
*A61K 39/275* (2006.01)

(52) U.S. Cl. ....................... 424/248.1; 424/9.1; 424/9.2; 424/184.1; 424/199.1; 424/232.1; 424/234.1

(58) Field of Classification Search ................. 424/9.1, 424/9.2, 184.1, 199.1, 232.1, 234.1, 248.1
See application file for complete search history.

(56) References Cited

U.S. PATENT DOCUMENTS 7,273,605 B2 * 9/2007 Laidlaw et al. ............. 424/93.2
2003/0138454 A1 * 7/2003 Hill et al. ................. 424/199.1

OTHER PUBLICATIONS

Calmette et al, Vaccination des Bovides Contre la Tuberculose et Methode Nouvelle de Prophylaxie de la Tuberculose Bovine, May 1924, Annales de L'Institut Pasteur, vol. 38, No. 5, pp. 371-398.
Baldwin et al, Immunology and Protective Efficacy of DNA Vaccines Encoding Secreted and Non-Secreted Forms of Mycobacterium tuberculosis Ag85A, 1999, Tubercle and Lung Disease, vol. 79, Issue 4, pp. 251-259.
Colditz et al, Efficacy of BCG vaccine in the prevention of tuberculosis: Meta-analysis of the published literature, Mar. 2, 1994, The Jounal of the American Medical Assocaton, vol. 271, No. 9, pp. 698-702.
Dunn et al, Fine Mapping of the Binding Sites of Monoclonal Antibodies Raised Against the Pk Tag, Apr. 1999, Journal of Immunological Methods, vol. 224, Issue 1-2, pp. 141-150.
Flynn et al, Immunology of Tuberculosis, 2001, Annual Review of Immunology, vol. 19, pp. 93-129.
Godkin et al, Evolution of Eptope-Specfic Memory CD4+ T Cells After Clearance of Hepatitis C Virus, Aug. 15, 2002, The Journal of Immunology, vol. 169, No. 4, pp. 2210-2214.
Goonetilleke et al, Enhanced Immunogenicity and Protective Efficacy Against Mycobacterium tuberculosis of Bacille Calmette-Gueérin Vaccine Using Mucosal Administration and Boosting with a Recombinant Modified Vaccinia Virus Ankara, Aug. 1, 2003, The Journal of Immunology, vol. 171, No. 3, pp. 1602-1609.
Harth et al, Novel Insights Into the Genetics, Biochemistry, and Immunocytochemistry of the 30-Kilodalton Major Extracellular Protein of Mycobacterium tuberculosis, Aug. 1996, Infection and Immunity, vol. 64, Issue 8, pp. 3038-3047.
Iezzi et al, Migration and Function of Antigen-primed Nonpolarized T Lymphocytes In Vivo, Apr. 2001, Brief Definitive Report, The Journal of Experimental Medicine, vol. 193, Issue 8, pp. 987-994.
Launois et al, T-Cell-Epitope Mapping of the Major Secreted Mycobacterial Antigen Ag85A in Tuberculosis and Leprosy, Sep. 1994, Infection and Immunity, vol. 62, No. 9, pp. 3679-3687.
Malin et al, Vaccinia Expression of Mycobacterium tuberculosis-Secreted Proteins: Tissue Plasminogen Activator Signal Sequence Enhances Expression and Immunogenicity of M. tuberculosis Ag85, Nov. 2000, Microbes and Infection, vol. 2, Issue 14, pp. 1677-1685.
McConkey et al, Enhanced T-cell Immunogenicity of Plasmid DNA Vaccines Boosed by Recombinant Modifed Vaccinia Virus Ankara in Humans, Jun. 2003, Nature Medicine, vol. 9, No. 6, pp. 729-735.
McShane et al, Protective Immunity against Mycobacterium tuberculosis Induced by Dendritic Cells Pulsed with both CD8+- and CD4+-T-Cell Epitopes from Antigen 85A, Mar. 2002, Infection and Immunity, vol. 70, No. 3, pp. 1623-1626.
McShane et al, Enhanced Immunogenicity of CD4+ T-Cell Responses and Protective Efficacy of a DNA-Modified Vaccinia Virus Ankara Prime-Boost Vaccination Regimen for Murine Tuberculosis, Feb. 2001, Infection and Immunity, vol. 69, No. 2, pp. 681-686.
McShane et al, Recombinant Modified Vaccinia Virus Ankara Expressing Antigen 85A Boosts BCG-Primed and Naturally Acquired Antimycobacterial Immunity in Humans, Nov. 2004, Nature Medicine, vol. 10, No. 11, pp. 1240-1244.
Mwau et al, A Human Immunodeficency Virus 1 (HIV-1) Clade A Vaccine in Clinical Trials: Stimulation of HIV-Specific T-Cell Responses by DNA and Recombinant Modified Vaccinia Virus Ankara (MVA) Vaccines in Humans, Apr. 2004, The Journal of General Virology, vol. 85, No. 4, pp. 911-919.

(Continued)

*Primary Examiner*—Rodney P. Swartz
(74) *Attorney, Agent, or Firm*—Wolf, Greenfield & Sacks, P.C.

(57) ABSTRACT

A method for generating a T cell immune response in a host involving administering a vectored vaccine comprising a non-replicating or replication impaired viral vector expressing the translation product of a mycobacterial antigen 85A gene. Vectored vaccines and uses thereof are also provided. Also provided is a method of inducing a CD8 and a CD4 memory T cell response against an antigen using an adenovirus vector expressing an antigen or an immunogenic fragment thereof.

10 Claims, 15 Drawing Sheets

OTHER PUBLICATIONS

Reece et al, A CD4+ T-Cell Immune Response to a Conserved Epitope in the Circumsporozoite Protein Correlates with Protection from Natural Plasmodium falciparum Infection and Disease, Apr. 2004, Nature Medicine, vol. 10, No. 4, pp. 406-410.

Reinhardt et al, Visualizing the Generation of Memory CD4 T Cells in the Whole Body, Mar. 1, 2001, Nature, vol. 410, No. 6824, pp. 101-105.

Rodrigues et al, Effect of BCG Revaccinaton on Incidence of Tuberculosis in School-Aged Children in Bazil: The BCG-REVAC Cluster-Randomised Trial, Oct. 8, 2005, The Lancet, vol. 366, Issue 9493, pp. 1290-1295.

Santosuosso et al, Mechanisms of Mucosal and Parenteral Tuberculosis Vaccinations: Adenoviral-Based Mucosal Immunization Preferentially Elicits Sustained Accumulation of Immune Protective CD4 and CD8 T Cells within the Airway Lumen, Jun. 15, 2005, The Journal of Immunology, vol. 174, No. 12, pp. 7986-7994.

Schneider et al, Enhanced Immunogenicity for CD8+ T cell Induction and Complete Protective Efficacy of Malaria DNA Vaccination by Boosting with Modified Vaccinia Virus Ankara, Apr. 1998, Nature Medicine, vol. 4, No. 4, pp. 397-402.

Sterne et al, Does the Efficacy of BCG Decline with Time Since Vaccination?, Mar. 1998, The International Journal of Tuberculosis and Lung Disease, vol. 2, No. 3, pp. 200-207.

Vordermeier et al, Immune Responses Induced in Cattle by Vaccination with a Recombinant Adenovirus Expressing Mycobacterial Antigen 85A and Mycobacterium bovis BCG, Feb. 2006, Infection and Immunity, vol. 74, No. 2, pp. 1416-1418.

Wang et al, Single Mucosal, but Not Parenteral, Immunization with Recombinant Adenoviral-Based Vaccine Provides Potent Protection from Pulmonary Tuberculosis, Nov. 15, 2004, The Journal of Immunology, vol. 173, No. 10, pp. 6357-6365.

Williams et al, Boosting with Poxviruses Enhances Mycobacterium bovis BCG Efficacy against Tuberculosis in Guinea Pigs, Jun. 2005, Infection and Immunity, vol. 73, No. 6, pp. 3814-3816.

http://www.ncbi.nlm.nih.gov/entrez/viewer.fcgi?db=protein&id=2950423, Accession No. CAA17868, retrieved Mar. 26, 2008, pp. 1-3.

http://www.ncbi.nlm.nih.gov/entrez/viewer.fcgi?db=nucleotide&val=38490370, Accession No. BX842584, retrieved Mar. 26, 2008, pp. 1-208.

Minutes of Oral Proceedings for EP 06700223.8 mailed Jun. 7, 2010.

* cited by examiner

Figure 1 (d)

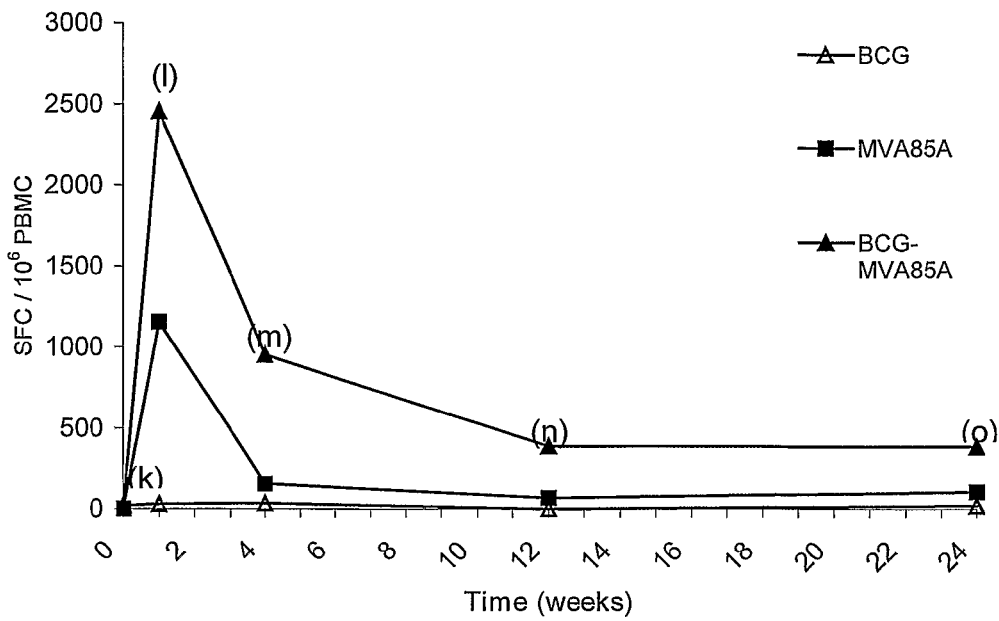

Figure 1 (e)

Median responses to PPD (Figure 1b)
   (a) B v BM, $P = 0.006$; M v BM, $P = 0.002$
   (b) B v M, $P = 0.021$; B v BM, $P = 0.001$; M v BM, $P = 0.047$
   (c) B v M, $P = 0.042$; M v BM, $P = 0.003$
   (d) B v BM, $P = 0.032$; M v BM, $P = 0.01$
   (e) B v BM, $P < 0.001$; M v BM, $P < 0.001$

Median responses to purified antigen 85 (Figure 1c)
   (f) B v BM, $P = 0.018$; M v BM, $P = 0.002$
   (g) B v M, $P = 0.003$; B v BM, $P < 0.001$; M v BM, $P = 0.024$
   (h) B v BM, $P < 0.001$; M v BM, $P = 0.004$
   (i) B v BM, $P = 0.003$; M v BM, $P = 0.033$
   (j) B v BM, $P < 0.001$; M v BM, $P < 0.001$

Median summed peptide pool responses (Figure 1d)
   (k) B v M, $P = 0.007$; M v BM, $P = 0.03$
   (l) B v M, $P < 0.001$; B v BM, $P < 0.001$; M v BM, $P = 0.015$
   (m) B v M, $P = 0.002$; B v BM, $P < 0.001$; M v BM, $P = 0.003$
   (n) B v M, $P = 0.003$; B v BM, $P < 0.001$; M v BM, $P = 0.003$
   (o) B v M, $P = 0.024$; B v BM, $P < 0.001$; M v BM, $P < 0.001$

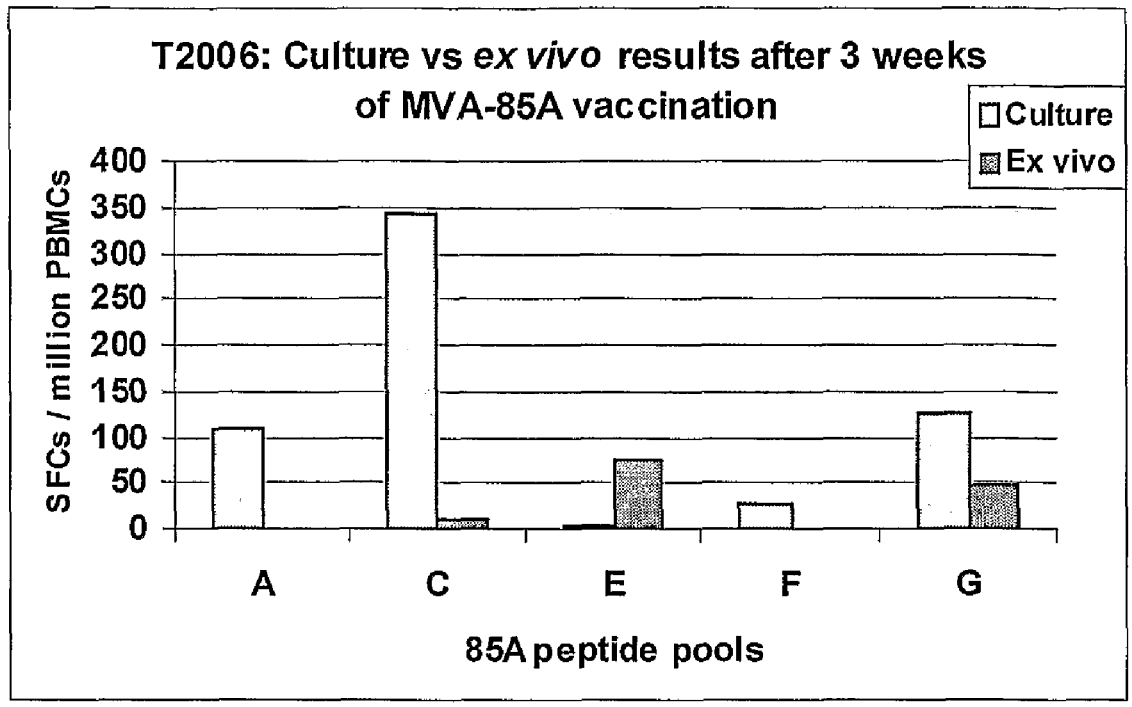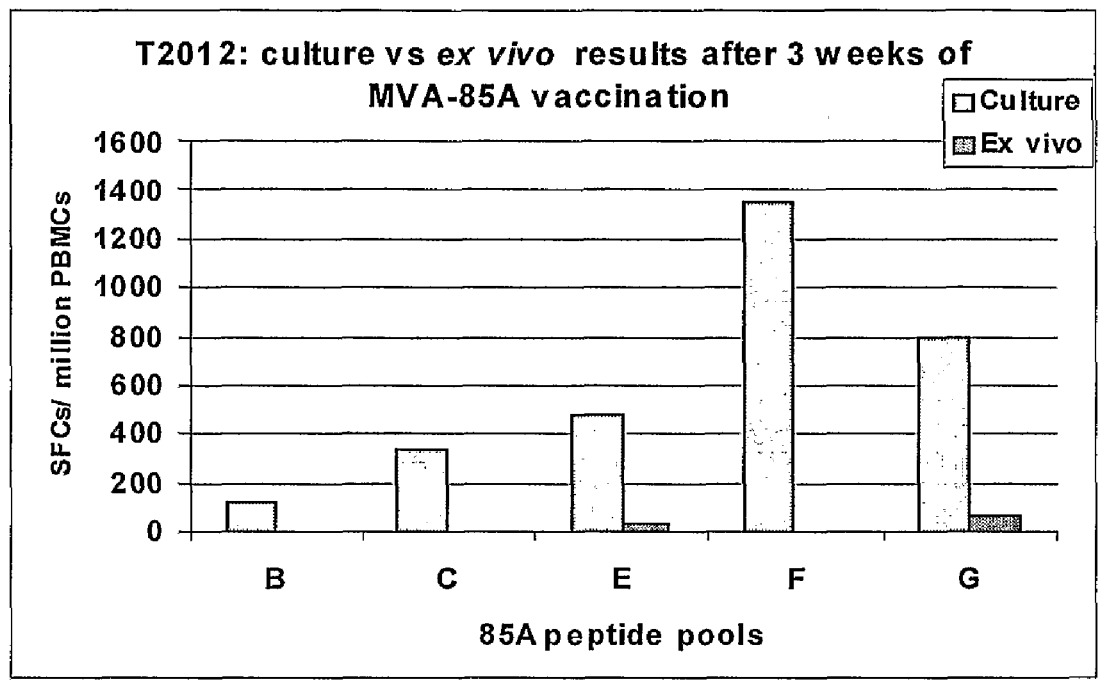

IFNγ response upon vaccination
mean levels of antigen-specific IFNγ secretion in a 3 day lymphocyte stimulation test (+ s.e.m.)

IFN-γ response after infection
Mean levels of antigen-specific IFN-γ secretion in a 3 day lymphocyte stimulation test (+ s.e.m). Week -5 = week 13 post primary immunistion; week -12 = week 6 post primary immunization; AUT = autopsy

SEQUENCE LISTING

<160> NUMBER OF SEQ ID NOS: 8

<210> SEQ ID NO 1
<211> LENGTH: 338
<212> TYPE: PRT
<213> ORGANISM: Mycobacterium tuberculosis

<400> SEQUENCE: 1

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala
```

<210> SEQ ID NO 2

<211> LENGTH: 1017
<212> TYPE: DNA
<213> ORGANISM: Mycobacterium tuberculosis

<400> SEQUENCE: 2

```
atgcagcttg ttgacagggt tcgtggcgcc gtcacgggta tgtcgcgtcg actcgtggtc      60
ggggccgtcg gcgcggccct agtgtcgggt ctggtcggcg ccgtcggtgg cacggcgacc     120
gcggggcat tttcccggcc gggcttgccg gtggagtacc tgcaggtgcc gtcgccgtcg      180
atgggccgtg acatcaaggt ccaattccaa agtggtggtg ccaactcgcc cgccctgtac     240
ctgctcgacg gcctgcgcgc gcaggacgac ttcagcggct gggacatcaa cacccccggcg    300
ttcgagtggt acgaccagtc gggcctgtcg gtggtcatgc cggtgggtgg ccagtcaagc     360
ttctactccg actggtacca gcccgcctgc ggcaaggccg gttgccagac ttacaagtgg     420
gagaccttcc tgaccagcga gctgccgggg tggctgcagg ccaacaggca cgtcaagccc     480
accgaagcg ccgtcgtcgg tctttcgatg gctgcttctt cggcgctgac gctggcgatc     540
tatcacccc agcagttcgt ctacgcggga gcgatgtcgg gcctgttgga ccccccag      600
gcgatgggtc ccaccctgat cggcctggcg atgggtgacg ctggcggcta caaggcctcc    660
gacatgtggg gcccgaagga ggacccggcg tggcagcgca cgacccgct gttgaacgtc     720
gggaagctga tcgccaacaa cacccgcgtc tgggtgtact gcggcaacgg caagccgtcg   780
gatctgggtg caacaacct gccggccaag ttcctcgagg gcttcgtgcg gaccagcaac    840
atcaagttcc aagacgccta caacgccggt ggcggccaca cggcgtgtt cgacttcccg     900
gacagcggta cgcacagctg ggagtactgg ggcgcgcagc tcaacgctat gaagcccgac    960
ctgcaacggg cactgggtgc cacgcccaac accgggcccg cgccccaggg cgcctag      1017
```

<210> SEQ ID NO 3
<211> LENGTH: 323
<212> TYPE: PRT
<213> ORGANISM: Mycobacterium tuberculosis

<400> SEQUENCE: 3

```
Met Gln Leu Val Asp Arg Val Arg Gly Ala Val Thr Gly Met Ser Arg
 1               5                  10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
        50                  55                  60

Ile Lys Val Gln Phe Gln Ser Gly Gly Ala Asn Ser Pro Ala Leu Tyr
 65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
```

-continued

```
                    165                 170                 175
Thr Leu Ala Ile Tyr His Pro Gln Gln Phe Val Tyr Ala Gly Ala Met
                180                 185                 190
Ser Gly Leu Leu Asp Pro Ser Gln Ala Met Gly Pro Thr Leu Ile Gly
            195                 200                 205
Leu Ala Met Gly Asp Ala Gly Gly Tyr Lys Ala Ser Asp Met Trp Gly
        210                 215                 220
Pro Lys Glu Asp Pro Ala Trp Gln Arg Asn Asp Pro Leu Leu Asn Val
225                 230                 235                 240
Gly Lys Leu Ile Ala Asn Asn Thr Arg Val Trp Val Tyr Cys Gly Asn
                245                 250                 255
Gly Lys Pro Ser Asp Leu Gly Gly Asn Asn Leu Pro Ala Lys Phe Leu
            260                 265                 270
Glu Gly Phe Val Arg Thr Ser Asn Ile Lys Phe Gln Asp Ala Tyr Asn
        275                 280                 285
Ala Gly Gly His Asn Gly Val Phe Asp Phe Pro Asp Ser Gly Thr
    290                 295                 300
His Ser Trp Glu Tyr Trp Gly Ala Gln Leu Asn Ala Met Lys Pro Asp
305                 310                 315                 320
Leu Gln Arg
```

<210> SEQ ID NO 4
<211> LENGTH: 969
<212> TYPE: DNA
<213> ORGANISM: Mycobacterium tuberculosis

<400> SEQUENCE: 4

```
atgcagcttg ttgacagggt tcgtggcgcc gtcacgggta tgtcgcgtcg actcgtggtc     60
ggggccgtcg gcgcggccct agtgtcgggt ctggtcggcg ccgtcggtgg cacggcgacc    120
gcggggcat  tttcccggcc gggcttgccg gtggagtacc tgcaggtgcc gtcgccgtcg    180
atgggccgtg acatcaaggt ccaattccaa gtggtggtg  ccaactcgcc cgccctgtac    240
ctgctcgacg gcctgcgcgc gcaggacgac ttcagcggct gggacatcaa caccccggcg    300
ttcgagtggt acgaccagtc gggcctgtcg gtggtcatgc cggtgggtgg ccagtcaagc    360
ttctactccg actggtacca gcccgcctgc ggcaaggccg gttgccagac ttacaagtgg    420
gagaccttcc tgaccagcga gctgccgggg tggctgcagg ccaacaggca cgtcaagccc    480
accggaagcg ccgtcgtcgg tctttcgatg gctgcttctt cggcgctgac gctggcgatc    540
tatcaccccc agcagttcgt ctacgcggga gcgatgtcgg gcctgttgga ccccctccag    600
gcgatgggtc ccaccctgat cggcctggcg atgggtgacg ctggcggcta caaggcctcc    660
gacatgtggg gcccgaagga ggacccggcg tggcagcgca acgacccgct gttgaacgtc    720
gggaagctga tcgccaacaa cacccgcgtc tgggtgtact gcggcaacgg caagccgtcg    780
gatctgggtg gcaacaacct gccggccaag ttcctcgagg gcttcgtgcg gaccagcaac    840
atcaagttcc aagacgccta caacgccggt ggcggccaca acggcgtgtt cgacttcccg    900
gacagcggta cgcacagctg ggagtactgg ggcgcgcagc tcaacgctat gaagcccgac    960
ctgcaacgg                                                            969
```

<210> SEQ ID NO 5
<211> LENGTH: 1176
<212> TYPE: DNA
<213> ORGANISM: Mycobacterium tuberculosis

```
<400> SEQUENCE: 5
tctgtacggg cccgtacggt accgagctcg gatctgcgcg ccgccaccat ggatgcaatg      60
aagagagggc tctgctgtgt gctgctgctg tgtggagcag tcttcgtttc gcccagccag     120
gaaatccatg cccgattcag aagaggatct atgcagcttg ttgacagggt tcgtggcgcc     180
gtcacgggta tgtcgcgtcg actcgtggtc ggggccgtcg gcgcggccct agtgtcgggt     240
ctggtcggcg ccgtcggtgg cacggcgacc gcggggggcat tttcccggcc gggcttgccg     300
gtggagtacc tgcaggtgcc gtcgccgtcg atgggccgtg acatcaaggt ccaattccaa     360
agtggtggtg ccaactcgcc cgccctgtac ctgctcgacg gcctgcgcgc gcaggacgac     420
ttcagcggct gggacatcaa caccccggcg ttcgagtggt acgaccagtc gggcctgtcg     480
gtggtcatgc cggtgggtgg ccagtcaagc ttctactccg actggtacca gcccgcctgc     540
ggcaaggccg gttgccagac ttacaagtgg gagaccttcc tgaccagcga gctgccgggg     600
tggctgcagg ccaacaggca cgtcaagccc accggaagcg ccgtcgtcgg tctttcgatg     660
gctgcttctt cggcgctgac gctggcgatc tatcacccccc agcagttcgt ctacgcggga     720
gcgatgtcgg gcctgttgga ccccctccag gcgatgggtc ccaccctgat cggcctggcg     780
atgggtgacg ctggcggcta caaggcctcc gacatgtggg gcccgaagga ggacccggcg     840
tggcagcgca acgaccccgct gttgaacgtc gggaagctga tcgccaacaa cacccgcgtc     900
tgggtgtact gcggcaacgg caagctgtcg gatctgggtg caacaacctg gccggccaag     960
ttcctcgagg gcttcgtgcg gaccagcaac atcaagttcc aagacgccta caacgccggt    1020
ggcggccaca acggcgtgtt cgacttcccg gacagcggta cgcacagctg ggagtactgg    1080
ggcgcgcagc tcaacgctat gaagcccgac ctgcaacgtg gatccattcc aaaccctttg    1140
ctgggattgg actgactgca gatatccatc acactg                              1176

<210> SEQ ID NO 6
<211> LENGTH: 367
<212> TYPE: PRT
<213> ORGANISM: Mycobacterium tuberculosis

<400> SEQUENCE: 6

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Gly Ser Met Gln Leu Val Asp Arg Val Arg Gly Ala Val Thr Gly Met
            35                  40                  45

Ser Arg Arg Leu Val Val Gly Ala Val Gly Ala Ala Leu Val Ser Gly
        50                  55                  60

Leu Val Gly Ala Val Gly Gly Thr Ala Thr Ala Gly Ala Phe Ser Arg
    65                  70                  75                  80

Pro Gly Leu Pro Val Glu Tyr Leu Gln Val Pro Ser Pro Ser Met Gly
                85                  90                  95

Arg Asp Ile Lys Val Gln Phe Gln Ser Gly Gly Ala Asn Ser Pro Ala
                100                 105                 110

Leu Tyr Leu Leu Asp Gly Leu Arg Ala Gln Asp Asp Phe Ser Gly Trp
            115                 120                 125

Asp Ile Asn Thr Pro Ala Phe Glu Trp Tyr Asp Gln Ser Gly Leu Ser
        130                 135                 140

Val Val Met Pro Val Gly Gly Gln Ser Ser Phe Tyr Ser Asp Trp Tyr
    145                 150                 155                 160
```

```
                                -continued

Gln Pro Ala Cys Gly Lys Ala Gly Cys Gln Thr Tyr Lys Trp Glu Thr
                165                 170                 175

Phe Leu Thr Ser Glu Leu Pro Gly Trp Leu Gln Ala Asn Arg His Val
            180                 185                 190

Lys Pro Thr Gly Ser Ala Val Val Gly Leu Ser Met Ala Ala Ser Ser
        195                 200                 205

Ala Leu Thr Leu Ala Ile Tyr His Pro Gln Gln Phe Val Tyr Ala Gly
    210                 215                 220

Ala Met Ser Gly Leu Leu Asp Pro Ser Gln Ala Met Gly Pro Thr Leu
225                 230                 235                 240

Ile Gly Leu Ala Met Gly Asp Ala Gly Gly Tyr Lys Ala Ser Asp Met
                245                 250                 255

Trp Gly Pro Lys Glu Asp Pro Ala Trp Gln Asn Asp Pro Leu Leu Asn
                260                 265                 270

Val Gly Lys Leu Ile Ala Asn Asn Thr Arg Val Trp Val Tyr Cys Gly
            275                 280                 285

Asn Gly Lys Leu Ser Asp Leu Gly Gly Asn Asn Leu Pro Ala Lys Phe
        290                 295                 300

Leu Glu Gly Phe Val Arg Thr Ser Asn Ile Lys Phe Gln Asp Ala Tyr
305                 310                 315                 320

Asn Ala Gly Gly His Asn Gly Val Phe Asp Phe Pro Asp Ser Gly
                325                 330                 335

Thr His Ser Trp Glu Tyr Trp Gly Ala Gln Leu Asn Ala Met Lys Pro
                340                 345                 350

Asp Leu Gln Arg Gly Ser Ile Pro Asn Pro Leu Leu Gly Leu Asp
            355                 360                 365

<210> SEQ ID NO 7
<211> LENGTH: 7
<212> TYPE: PRT
<213> ORGANISM: Artificial Sequence
<220> FEATURE:
<223> OTHER INFORMATION: PK tag

<400> SEQUENCE: 7

Pro Asn Pro Leu Gly Leu Asp
1               5

<210> SEQ ID NO 8
<211> LENGTH: 8
<212> TYPE: PRT
<213> ORGANISM: Artificial Sequence
<220> FEATURE:
<223> OTHER INFORMATION: PK tag

<400> SEQUENCE: 8

Pro Asn Pro Leu Leu Gly Leu Asp
1               5
```

COMPOSITIONS FOR IMMUNIZING AGAINST MYCOBACTERIUM

RELATED APPLICATIONS

This Application is the U.S. National Stage of PCT Application Ser. No. PCT/GB2006/000023, filed Jan. 5, 2006, which claims the benefit under 35 U.S.C. §119 and 35 U.S.C. §365 to United Kingdom Patent Application Serial No. 0500102.9, filed Jan. 5, 2005, and the benefit under 35 U.S.C. §119(e) of U.S. Provisional Patent Application Ser. No. 60/649,804, filed Feb. 3, 2005, all of which are incorporated herein by reference in their entirety.

SEQUENCE LISTING

The text file isii0101pusa.txt, created Jun. 3, 2008, and of size 14 KB, filed therewith, is hereby incorporated by reference.

The present invention relates to a method for generating a T cell immune response in a host. The method involves the step of administering a vectored vaccine comprising a non-replicating or replication impaired viral vector expressing the translation product of a mycobacterial antigen 85A gene (also referred to herein as the "Ag85A" gene).

All publications, patents and patent applications cited herein are incorporated in full by reference.

BACKGROUND TO THE INVENTION

Tuberculosis is caused by the respiratory pathogen *Mycobacterium tuberculosis* and kills 2 million people each year, predominantly in the developing world. The only licensed vaccine against *M. tuberculosis*, bacille Calmette-Guerin (BCG) (Calmette, A., C. Guerin. (1924) Ann. Inst. Pasteur. 38:371), is an attenuated strain of *Mycobacterium bovis*, which in developing countries is typically administered intradermally as a single dose to newborn infants. Review of many studies suggests that BCG vaccination is protective against childhood meningeal tuberculosis and systemic forms of the disease. However, protective efficacy is variable (ranging from 0-80%) (Colditz, G. A. et al. (1994). JAMA 271:698) against adult pulmonary disease, the major global cause of tuberculosis mortality, and wanes with time (Sterne, J. A. et al. (1998) Int. J. Tuberc. Lung Dis. 2:200). The basis of the variability is uncertain. Even so, 80% of infants throughout the world receive BCG each year.

*Mycobacterium tuberculosis* is an intracellular pathogen, protective efficacy against which is associated with the maintenance of a strong cell-mediated response to infection involving both CD4+ and CD8+ T cells and the ability to respond with Th1-type cytokines, particularly IFN-γ (Flynn, J. L., J. Chan. (2001) Annu. Rev. Immunol. 19:93). BCG vaccination induces IFN-γ-secreting T cells, predominately of the CD4+ T cell phenotype, that cross-react with *M. tuberculosis* proteins (Launois P et al, (1994) Infection and Immunity 62(9):3679-87). Recent studies suggest that BCG delivered parenterally may fail to induce T cell immune responses in the lung mucosa, which may be critical for protection against pulmonary disease.

There is therefore a need to develop further vaccines against Mycobacterial disease.

SUMMARY OF THE INVENTION

Surprisingly, it has now been found that viral vectors expressing Mycobacterial antigen 85A (Ag85A) can induce a T cell immune response in a human patient when administered as an immunogenic composition. Therefore, the invention provides a method of inducing a T cell immune response against a mycobacterial antigen in a human patient comprising the step of administering an immunogenic composition comprising a non-replicating or replication impaired viral vector expressing the translation product of a mycobacterial Ag85A gene to the patient. Preferably, the immunogenic composition is a vectored vaccine. This novel vaccine approach significantly improves the magnitude and duration of the T cell immune response. Preferably, the T cell response is a memory T cell response.

The 85A antigen (Ag85A) (Accession Nos. CAA17868 and BX842584) is a member of the Ag 85 complex. This is a family of proteins comprising Ags 85A, 85B, and 85C secreted by *M. tuberculosis*, BCG, and many other species of mycobacteria (Harth, G. et al., (1996) Infect. Immun. 64:3038-3047). Antigen 85A (Ag85A) is highly conserved amongst all mycobacterial species and is immunodominant in animal and human studies. Ag 85A (Ag85A) is encoded by the fbpA gene. The 85A antigen (Ag85A) from *Mycobacterium tuberculosis* is listed in SEQ ID NOs 1 and 2 herein).

Recent strategies to induce enhanced T cell responses in tuberculosis vaccine research have harnessed recombinant DNA technology, using plasmid, bacterial, or viral vectors and recombinant protein to express *M tuberculosis* antigens. Vaccination of mice with Ag85A DNA boosted with a MVA vector expressing Ag85A has been shown to afford a degree of protection equivalent to BCG following *M. tuberculosis* challenge (McShane, H. et al., (2002). Infect. Immun. 70:1623-1626). However, immune responses generated by single or repeated immunization with the recombinant MVA vector alone were weak.

For long term protection against mycobacterial disease such as tuberculosis it is considered important to maintain "memory T cells", which can continue to stimulate protective immunity for decades.

Memory immune responses are classically attributed to the reactivation of long-lived, antigen-specific T lymphocytes that arise directly from differentiated effector T cells and persist in a uniformly quiescent state. Effector and memory T cells are thought to be distributed to all tissues in the body, particularly epithelial surfaces (such as the skin and gut) where pathogens are likely to be re-encountered.

Memory T cells have been shown to be heterogeneous and to comprise at least two subsets, endowed with different migratory capacity and effector function (Reinhardt, R. L. et al., (2001) Nature. 410, 101-105). Cells of the first subset resemble the effector cells generated in the primary response in that they lack the lymph node-homing receptors L-selectin and CCR7 and express receptors for migration into inflamed tissues. Upon re-encounter with antigen, these "effector memory T cells" (TEM) can rapidly produce IFN-γ or IL-4 or release pre-stored perforin. Cells of the second subset express L-selectin and CCR7 and lack immediate effector function. These "central memory T cells" (TCM) have a low activation threshold and, upon restimulation in secondary lymphoid organs, proliferate and differentiate to effectors (Iezzi, G. et al., (2001). J. Exp. Med. 193, 987-994).

The present inventors have found that a replication impaired viral vector expressing Ag 85A (Ag85A) (in this case, exemplified with "MVA85A") can induce high levels of antigen specific interferon-γ secreting memory T cells—both effector memory and central memory T cells—when used alone in BCG naïve healthy volunteers.

New immunological assays for measuring and quantifying T cell responses have been established over the last 10 years.

The present inventors utilised the interferon-gamma (IFN-γ) ELISPOT assay as the main immunological readout for clinical trials with MVA85A, because the secretion of IFN-γ from antigen specific T cells is the best available correlate of protection against *M. tuberculosis*. Furthermore, the ELISPOT assay is a very reproducible and sensitive method of quantifying the number of IFN-γ secreting antigen specific T cells.

The present inventors utilised two ELISPOT assays: the ex-vivo (fresh) ELISPOT assay, wherein peripheral blood mononuclear cells (PBMC) are incubated for 18 hours with antigen to determine levels of CCR7− circulating effector T cells, and the cultured ELISPOT assay, wherein PBMC are incubated with antigen for 10-14 days to measure levels of CCR7+ central memory T cells (Godkin et al, The Journal of Immunology, p. 2210-2214 (2002)).

The present inventors have discovered that vaccination with MVA85A induces a strong central memory T cell response specific for antigen 85A (Ag85A) which is still detectable 3 weeks after vaccination, when the circulating effector T cell response is almost undetectable.

This is the first demonstration that the long-term central memory T cell population may be significantly enhanced in a patient by the administration of an immunogenic composition expressing a mycobacterial antigen.

As used herein, the term "memory T cell" is intended to include both the CCR7− (effector memory T cells) and CCR7+ (central memory T cells) subpopulations of T cells. This definition also includes both class II-restricted CD4 memory T cells and class I-restricted CD8 memory T cells. Preferably, the memory T cells induced by the vectored vaccines of the invention are characterised by cell surface expression of CCR7+. These are referred to herein as central memory T cells.

Preferably, the memory T cell response induced by the immunogenic compositions of the invention is a protective T cell response. A protective immune response may be measured by immunoassay of IFN-γ secretion, preferably from antigen specific T cells. Preferably, the memory T cell response is long lasting and persists for at least 1, 2, 5, 10, 15, 20, 25 or more years. Most preferably, the protective immune response is lifelong.

Preferably, the Ag85A gene is expressed in a viral vector. Preferably, the Ag85A gene is expressed in a non-replicating or replication-impaired viral vector.

The term "vectored vaccines" is well known in the art. The vector used in the method according to the invention is a non-replicating or replication-impaired viral vector. The term "non-replicating" or "replication-impaired" as used herein means not capable of replication to any significant extent in the majority of normal human cells. Viruses which are non-replicating or replication-impaired may have become so naturally (i.e. they may be isolated as such from nature) or artificially e.g. by breeding in vitro or by genetic manipulation, for example deletion of a gene which is critical for replication. There will generally be one or a few cell types in which the viruses can be grown, such as CEF cells for modified virus Ankara (MVA). In general, the viral vector should be capable of stimulating a T cell response.

Examples of viral vectors that are useful in this context are vaccinia virus vectors such as MVA or NYVAC. A preferred viral vector is the vaccinia strain MVA or a strain derived from MVA. Alternatives to vaccinia vectors include other poxvirus vectors including avipox vectors such as fowlpox or canarypox vectors. Particularly suitable as an avipox vector is a strain of canarypox known as ALVAC (commercially available as Kanapox), and strains derived from ALVAC, and also a fowlpox strain known as FP9. Further alternatives are alphavirus vectors, adenoviral vectors, herpes viral vectors, flavivirus vectors, retroviral vectors and influenza virus vectors.

For example, the vector may be a non-human adenovirus vector. It has surprisingly been found that the use of an adenovirus vector induces a very strong CD8 memory T cell response in addition to a very strong CD4 memory T cell response. The induction of both a CD8 and a CD4 memory T cell response by the same vaccine is likely to be of benefit in both the prophylaxis and treatment of mycobacterial disease. A method of inducing a CD8 and a CD4 memory T cell response against an antigen using an adenovirus vector expressing the antigen or an immunogenic fragment thereof is therefore also included within the scope of this application. The antigen expressed by the adenovirus vector is preferably a mycobacterial antigen as described above, most preferably Ag85A, but may alternatively be any other suitable antigen.

Also encompassed within the scope of the invention is the use of an adenovirus vector expressing an antigen or immunogenic fragment thereof in the manufacture of a medicament for inducing a CD8 and a CD4 memory T cell response against the antigen. Preferably, the invention provides the use of an adenovirus vector expressing a mycobacterial antigen or immunogenic fragment thereof in the manufacture of a medicament for the treatment or prophylaxis of a mycobacterial disease. The antigen is preferably a mycobacterial antigen as described above, most preferably Ag85A, but may alternatively be any other suitable antigen.

It is preferred that the viral vector is incapable of causing a serious infection in the human patient.

Replication of a virus is generally measured in two ways: 1) DNA synthesis and 2) viral titre. More precisely, the term "non-replicating or replication-impaired" as used herein and as it applies to poxviruses means viruses which satisfy either or both of the following criteria:

1) exhibit a 1 log (10 fold) reduction in DNA synthesis compared to the Copenhagen strain of vaccinia virus in MRC-5 cells (a human cell line);

2) exhibit a 2 log reduction in viral titre in HELA cells (a human cell line) compared to the Copenhagen strain of vaccinia virus.

Examples of poxviruses which fall within this definition are MVA, NYVAC and avipox viruses, while a virus which falls outside the definition is the attenuated vaccinia strain M7.

The invention also provides for the use of an immunogenic composition comprising a non-replicating or replication impaired viral vector expressing the translation product of a mycobacterial Ag85A gene in the manufacture of a medicament for the treatment or prevention of mycobacterial disease in a human patient. Preferably the immunogenic composition is a vectored vaccine. The immunogenic composition and vectored vaccine act by inducing a T cell immune response in the patient.

Vaccines according to the invention may either be prophylactic (i.e. to prevent infection), post-exposure (i.e. to treat after infection but before disease) or therapeutic (i.e. to treat disease), but will typically be prophylactic or post-exposure.

Mycobacterial diseases which can be treated or prevented by the vectored vaccine of the present invention include; tuberculosis, leprosy, *Mycobacterium avium* infection, non-tuberculosis mycobacterial infection, Buruli ulcer, *Mycobacterium bovis* infection or disease, *Mycobacterium paratuberculosis* infection or related disease. Other diseases (i.e., not mycobacterial diseases) include inflammatory bowel disease, Crohns disease, autoimmune disease, cancer, bladder cancer, smallpox and monkeypox.

Specialized viral vector constructs may be used to facilitate the preparation and utility of the vectored vaccine. All the vector constructs described herein form aspects of the invention. Vectored vaccines comprising these viral constructs are also encompassed as aspects of the invention.

For example, one or more antigen genes may be truncated at the C-terminus or the N-terminus of the gene. This may have the effect of facilitating cloning and construction of the vectored vaccine, and alternatively or additionally, may lead to increased efficacy. Methods for truncation will be known to those of skill in the art. The simplest way to effect truncations of this type is to use the various well-known techniques of genetic engineering to delete selectively the encoding nucleic acid sequence at either end of the antigen gene, and then insert the desired coding sequence into the viral vector. For example, truncations of the candidate protein are created using 3' and/or 5' exonuclease strategies selectively to erode the 3' and/or 5' ends of the encoding nucleic acid, respectively. Preferably, the wild type gene sequence is truncated such that the expressed antigen is truncated by 1, 2, 3, 4, 5, 6, 7, 8, 9, 10, 11, 12, 13, 14, 15, 16, 17, 18, 19, 20 or more amino acids relative to the parent antigen. Most preferably, antigen gene is Ag85A which is truncated by 15 amino acids at the C-terminus relative to the wild type Ag85A antigen (SEQ ID NO:3, the expression product of SEQ ID NO:4).

The antigens suitable for use in the invention also include fragments of the parent antigen, provided that those fragments have an antigenic determinant or epitope in common with or are immunologically identifiable with the parent antigen. Polynucleotides encoding these fragments are also suitable for use in the immunogenic compositions and vectored vaccines of the invention.

As used herein, the term "fragment" refers to a polypeptide having an amino acid sequence that is the same as part, but not all, of the amino acid sequence of the parent antigen from which it is derived or one of their functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

The antigen genes of the invention may also encode the variants or the functional equivalents of the parent antigen. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned antigen gene sequences by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

Alternatively or in addition to the use of a gene truncation, the gene encoding the antigen may comprise a nucleic acid encoding a tag polypeptide such that this is covalently linked to the antigen upon translation. Preferably the tag polypeptide is selected from the group consisting of a PK tag, a FLAG tag, a MYC tag, a polyhistidine tag or any tag that can be detected by a monoclonal antibody. Other examples will be clear to the person of skill in the art. If used, the PK tag preferably has the sequence Pro-Asn-Pro-Leu-Gly-Leu-Asp (SEQUENCE ID NO: 7). A tag of this type may facilitate detection of antigen expression, and clones expressing the antigen, and alternatively or additionally, may lead to increases in efficacy.

The nucleic acid encoding the tag polypeptide may be positioned such that, following translation, the tag is located at the C-terminus or the N-terminus of the expressed antigen or may be internal to the expressed antigen. Preferably, the tag is located at the C-terminus of the expressed antigen. Nucleotides encoding a linker sequence may be inserted between the nucleic acid encoding the tag polypeptide and the nucleic acid encoding the expressed antigen. Preferably, the linker sequence, when expressed, comprises the amino acids Gly-Ser-Ile. More preferably, the amino acids Gly-Ser-Ile are inserted between the N-terminal antigen sequence and the tag of the expressed antigen. Most preferably, the expressed antigen is Ag85a (Ag85A) and a PK tag is located at the C-terminus of the Ag85a (Ag85A) gene.

A gene encoding an antigen can also include a leader sequence. The leader sequence may affect processing of the primary transcript to mRNA, mRNA stability or translation efficiency. Preferably, the leader sequence enhances expression and/or immunogenicity of the antigen. Enhanced immunogenicity can be determined through e.g. cultured and ex vivo ELISPOT assays. An enhanced level of expression can be determined by e.g. using a monoclonal antibody to detect the amount of protein produced. Preferably, expression and/or immunogenicity are enhanced by 2-fold, 3-fold or more when compared to antigen expressed without the leader sequence. An example of a suitable leader sequence is t-PA (tissue plasminogen activator) (Malin A. S. et al. (2000) Microbes Infect. 2000 November; 2(14):1677-85).

Preferably, the viral vector construction comprises a C-terminally truncated sequence of Ag85A fused to a TPA leader sequence. In a still further preferred embodiment, the viral vector of the invention expresses a C-terminally truncated sequence of Ag85A fused to a TPA leader sequence and to a PK tag sequence. Preferably, the leader sequence is fused to the N-terminus of the antigen and the tag sequence is fused either internally or to the C-terminus of the protein. In an especially preferred embodiment, the viral vector construction comprises a polynucleotide encoding Ag85a (Ag85A) C-terminally truncated by 15 amino acids fused to a TPA sequence and with a C-terminal PK tag of sequence Pro-Asn-Pro-Leu-Leu-Gly-Leu-Asp wherein the amino acid residues Gly-Ser-Ile are present between the Ag85A sequence and the PK tag (SEQ ID NO:5). Preferably, the expression product of the viral vector has the amino acid sequence of SEQ ID NO:6.

The protective T cell effect noted by the inventors has been found to be particularly potent in human patients who have been previously exposed to a mycobacterial antigen. Heterologous prime-boost immunisation strategies induce higher levels of effector T cell responses in animals and humans than homologous boosting with the same vaccine (Schneider, J. et al. (1998) Nat. Med. 4, 397-402, McShane, H. et al (2001) Infect. Immun. 69, 681-686).

The mechanism underlying the gradual loss of effectiveness of BCG as the (neonatally-inoculated) individual reaches 10 to 15 years of age is poorly understood. One possible assumption is that immunity generated by BCG has disappeared and the individual becomes equivalent to a naive host who can be vaccinated with a new candidate vaccine designed to induce primary immunity. Although repeated vaccination with BCG does not appear to further enhance protection against TB (ref Rodrigues L et al, Lancet 2005), incorporating BCG into a heterologous prime-boost regime would retain the protective effects of BCG. The immunogenicity and protective efficacy of boosting BCG with viral vectors expressing antigen 85A (Ag85A) in several animal models has previously been documented (Goonetilleke, N. P. et al. (2003) J. Immunol. 171, 1602-1609; Williams A et al, Infection and Immunity (73(6):3814-6 (2005)), but the induction of a protective memory T cell response was not documented.

Therefore, the invention also provides a method for raising a T cell immune response in a human patient, comprising the step of administering at least one mycobacterial antigen to a patient in combination with a vectored vaccine comprising a non-replicating or replication impaired viral vector expressing the translation product of a mycobacterial 85a (Ag85A) gene. Preferably, the T cell immune response is a memory T cell immune response.

The invention also provides the use of: (a) at least one mycobacterial antigen; and (b) a vectored vaccine comprising a non-replicating or replication impaired viral vector expressing the translation product of a mycobacterial 85a (Ag85A) gene, in the manufacture of a medicament for administration to a patient to induce a T cell immune response.

The vectored vaccine comprising a non-replicating or replication impaired viral vector expressing the translation product of a mycobacterial 85a (Ag85A) gene and the mycobacterial antigen(s) may be administered simultaneously, sequentially or separately. For example, the mycobacterial antigen(s) may be administered to prime the patient before or after administration of the vectored vaccine to boost the patient's immune response to the vectored vaccine.

Furthermore, the invention also provides a method of inducing a T cell immune response in a human patient comprising the step of administering an immunogenic composition comprising a non-replicating or replication impaired viral vector expressing the translation product of a mycobacterial Ag85A gene to the human patient, wherein the patient has been pre-exposed to at least one mycobacterial antigen. Preferably, the T cell immune response is a memory T cell immune response.

The invention also provides for the use of an immunogenic composition comprising a vectored vaccine comprising a non-replicating or replication impaired viral vector expressing the translation product of a mycobacterial 85a (Ag85A) gene, in the manufacture of a medicament for the treatment or prevention of mycobacterial disease in a human patient which has been pre-exposed to a mycobacterial antigen.

The mycobacterial antigen may be from *M. tuberculosis* and/or may be from one or more other mycobacteria such as *M. avium-intracellulare, M. kansasii, M. marinum* and/or *M. ulcerans*. Where the patient has been pre-exposed to only one antigen, the antigen may be an antigen that confers a protective immune response against mycobacterial infection. In one embodiment of the invention, the antigen to which the patient has been pre-exposed is not Ag85A.

Alternatively or additionally, the patient may have been pre-exposed to one or more mycobacteria themselves. For example, pre-exposure of a patient to at least one mycobacterial antigen may comprise prior exposure to *M. tuberculosis*. Alternatively or additionally, pre-exposure of a patient to at least one mycobacterial antigen may comprise prior exposure to environmental mycobacteria such as *M. avium-intracellulare, M. kansasii, M. marinum* and/or *M. ulcerans*. Preferably, the patient is latently infected with the mycobacteria. For example, the patient may have been pre-exposed to *M. tuberculosis* and be latently infected with tuberculosis. Where the medicament is for the treatment of a patient who is latently infected with the mycobacteria, the treatment preferably eradicates the mycobacterial infection.

Alternatively or additionally, pre-exposure may comprise neonatal or pre-vaccination with BCG. The present inventors have found that in volunteers who had been vaccinated previously with BCG and who then received a boosting dose of the vectored vaccine of the present invention, substantially higher levels of antigen specific interferon-γ secreting T cells were induced, and at 24 weeks after vaccination these levels were 5-30 times greater than in vaccinees administered a single BCG vaccination.

Accordingly, this aspect of the invention provides a method of inducing a T cell immune response in a human patient, comprising the steps of exposing the patient to at least one mycobacterial antigen, and boosting the immune response by administering a boosting composition comprising an immunogenic composition comprising a non-replicating or replication impaired viral vector expressing the translation product of a mycobacterial 85a (Ag85A) gene.

This aspect of the invention also relates to a method for generating a T cell immune response in a human patient, comprising the steps of;

i) exposing the patient to at least one mycobacterial antigen;

ii) administering to said patient at least one dose of a boosting composition comprising a vectored vaccine comprising a non-replicating or replication impaired viral vector expressing the translation product of a mycobacterial 85a (Ag85A) gene.

In one embodiment of the invention, where the patient is exposed to only one mycobacterial antigen in step i), the antigen is an antigen that confers a protective immune response, but is not Ag85A.

Step i) may be performed on the patient at any age, for example, neonatally, during infancy, during adolescence or during adulthood. Preferably, the patient is neonatally exposed to the at least one mycobacterial antigen.

Administration of the immunogenic composition may occur at least 1, 2, 3, 4, 5, 6, 7, 8, 9 or 10 or more weeks or 0.25, 0.5, 0.75, 1, 5, 10, 15, 20, 25, 30, 35 or 40 or more years after pre-exposure to at least one mycobacterial antigen. Preferably, where step i) is performed when the patient is in infancy, step ii) is performed during infancy or adolescence.

Where step ii) comprises administering more than one dose of a boosting composition to the patient, the more than one doses may be administered over a short time period of over a long time period. For example, the doses of boosting composition may be administered over a period of hours, days, weeks, months or years. For example, the second boosting dose may be administered between 0.5 and 24 hours after the first boosting dose, between 1 day and 7 days after the first boosting dose, between 1 week and 1 month after the first boosting dose, between 1 month and 6 months after the first boosting dose, between 6 months and 1 year after the first boosting dose, or between 1 to 2, 2 to 5, 6 to 10, or more than 10 years after the first boosting dose. These time intervals preferably also apply mutatis mutandis to the period between any subsequent doses.

In a second aspect of the invention, in addition to the immune response induced against the 85a (Ag85A) antigen, the viral vector stimulates a vector specific T-cell response. According to this aspect of the invention, administration of the vectored vaccine of the invention promotes a T cell immune response against the virus from which the viral vector is derived. For example, use of an MVA vector in the vectored vaccine of the invention promotes a T cell immune response against vaccinia virus. Preferably, this T cell response is a protective T cell response. An effect of this type has not been reported previously and is clearly advantageous in that the vectored vaccine has a dual role; firstly in protecting against mycobacterial diseases, and second in protecting against a disease mediated by viruses related to the vector. In the case of the MVA vector, such a disease is smallpox.

Virally derived diseases which can be treated or prevented by the vectored vaccine of the present invention will be clear to those of skill in the art; examples include smallpox, monkeypox and disseminated vaccinia infection.

Accordingly, this aspect of the invention provides a method of inducing a T cell immune response against a mycobacterial antigen and a virus in a human patient comprising the step of administering an immunogenic composition comprising a non-replicating or replication impaired viral vector expressing the translation product of a mycobacterial Ag85A gene to the human patient. Preferably, the T cell immune response is a memory T cell response.

This aspect of the invention also provides the use of an immunogenic composition comprising a non-replicating or replication impaired viral vector expressing the translation product of a mycobacterial Ag85A gene in the manufacture of a medicament for the induction of a T cell immune response against a mycobacterial antigen and a virus in a human patient.

The vaccines of the invention deliver an immunologically effective amount of at least one antigen to a patient. By 'immunologically effective amount', it is meant that the administration of that amount to an individual, either in a single dose or as part of a series, is effective for treatment or prevention. This amount varies depending upon the health and physical condition of the individual to be treated, age, the capacity of the individual's immune system, the degree of protection desired, the formulation of the vaccine, the treating doctor's assessment of the medical situation, and other relevant factors. It is expected that the amount will fall in a relatively broad range that can be determined through routine trials.

In a third aspect of the invention, the viral vector may further express the translation product of one or more additional antigen genes which can be used to induce an antigen specific immune response against such additional antigens. The immune response may be a CD8+, CD4+ and/or antibody response. Preferably, the one or more additional antigen genes is/are derived from *M. tuberculosis, Plasmodium* sp, influenza virus, HIV, *Hepatitis C* virus, *Cytomegalovirus, Human papilloma* virus, malaria, leishmania parasites or, preferably, any mycobacteria spp. Preferably, the one or more additional antigen genes encode an antigen selected from the group consisting of; an antigen of the antigen 85 family from any Mycobacterium or any antigen expressed by mycobacteria spp.; more preferably one or more latency antigens such as the 16kDa antigen or heparin-binding heamagglutinin (HBHA) or ESAT6 or the fusion protein known as 72F.

It is also envisaged that the additional antigen may be endogenously derived such that the immune response induced is directed against a tumour. Endogenously derived antigens which are suitable for use with the present invention are; human heat shock proteins and tumour associated antigens such as CEA, PSA, Muc-1, Her2neu.

The viral vector may be designed to express the Ag85A gene and the one or more additional antigen genes as an epitope string. Advantageously, the epitopes in a string of multiple epitopes are linked together without intervening sequences so that unnecessary nucleic acid and/or amino acid material is avoided. The creation of the epitope string may preferably be achieved using a recombinant DNA construct that encodes the amino acid sequence of the epitope string, with the DNA encoding the Ag85A in the same reading frame as the DNA encoding the additional antigen(s). Alternatively, the Ag85A and the additional antigen(s) may be expressed as separate polypeptides.

This aspect of the invention also provides the use of a vectored vaccine comprising a non-replicating or replication impaired viral vector expressing the translation product of a mycobacterial Ag85A gene and the translation product of at least one additional antigen or epitope gene in the manufacture of a medicament for the treatment of prevention of both mycobacterial disease and at least one additional disease in a human patient by inducing a T cell response in the patient.

According to this aspect of the invention, the vectored vaccine may be used to protect against both mycobacterial disease, and against one or more diseases selected from the group consisting of HIV, malaria, and smallpox through the induction of a T cell immune response in a human patient, preferably a memory T cell immune response.

Although the vectored vaccine of the present invention may be used in isolation, it may also be combined with other vaccination or therapeutic regimens for treating or preventing an additional disease. Therefore, as well as providing the vectored vaccines as described above, the invention provides a composition comprising a vectored vaccine of the invention and one or more further antigens or epitopes derived from a disease-causing agent.

Antigens and epitopes suitable for use in the compositions of the invention may be of bacterial or viral origin. Suitable antigens may be further classified as protein antigens, carbohydrate antigens or glycoconjugate antigens. The compositions of the invention may include one or more farther antigens or epitopes. Examples are:

a different mycobacterial antigen or eptiope.

an HIV antigen or epitope.

a Plasmodium antigen or epitope.

a malaria antigen or epitope.

a saccharide antigen from *Streptococcus pneumoniae*.

a protein antigen from *S. pneumoniae* (e.g. from PhtA, PhtD, PhtB, PhtE, SpsA, LytB, LytC, LytA, Sp125, Sp101, Sp128, Sp130 and Sp133).

an antigen or epitope from hepatitis A virus, such as inactivated virus.

an antigen or epitope from hepatitis B virus, such as the surface and/or core antigens.

an antigen or epitope from hepatitis C virus.

a saccharide antigen from *Haemophilus influenzae* type b.

polio antigen(s) or epitopes such as in IPV.

diphtheria vaccine or its constituent epitopes or antigens or toxoid.

tetanus vaccine or its constituent epitopes or antigens or toxoid.

measles, mumps and/or rubella antigens or epitopes.

influenza antigen(s) or epitopes such as the haemagglutinin and/or neuraminidase surface proteins. The flu antigen may be selected from a pandemic strain, e.g., from avian flu, e.g., strain H5N1.

an antigen or epitope from *Staphylococcus aureus*.

a cancer antigen or epitope.

Where a saccharide antigen is used, it is preferably conjugated to a carrier in order to enhance immunogenicity. Toxic protein antigens may be detoxified where necessary e.g. by chemical and/or genetic means.

Saccharide antigens are preferably in the form of conjugates. Preferred carrier proteins for conjugates are bacterial toxins or toxoids, such as diphtheria toxoid or tetanus toxoid. The CRM197 mutant of diphtheria toxin is a particularly preferred carrier, as is a diphtheria toxoid. Other suitable carrier proteins include the *N. meningitidis* outer membrane protein, synthetic peptides, heat shock proteins, pertussis proteins, cytokines, lymphokines, hormones, growth factors, artificial proteins comprising multiple human CD4+ T cell epitopes from various pathogen-derived antigens such as the N19 protein, protein D from *H. influenzae*, pneumococcal surface protein PspA, pneumolysin, iron-uptake proteins, toxin A or B from *C. difficile*, etc.

Further antigens in the composition will typically be present at a concentration of at least 1 μg/ml each. In general, the concentration of any given antigen will be sufficient to elicit an immune response against that antigen.

As an alternative to using further protein antigens in the mixture, nucleic acid encoding the antigen may be used. Protein components of the mixture may thus be replaced by nucleic acid (preferably DNA e.g. in the form of a plasmid) that encodes the protein. Similarly, compositions of the invention may comprise proteins which mimic saccharide antigens e.g. mimotopes or anti-idiotype antibodies.

Furthermore, the invention also provides a composition comprising a vectored vaccine of the invention and one or more antimicrobial compounds. Examples of antimicrobials suitable for use in the compositions of the invention are anti-tuberculous chemotherapeutics such as rifampicin, isoniazid, ethambutol, pyrizinamide, etc.

Accordingly, the invention provides a method of raising a T cell immune response against at least one antigen in a human patient comprising the step of administering a vectored vaccine comprising a non-replicating or replication impaired viral vector expressing the translation product of a mycobacterial Ag 85A (Ag85A) gene, in combination with at least one further antigen and/or antimicrobial, to the patient.

The invention also provides the use of: (a) a vectored vaccine comprising a non-replicating or replication impaired viral vector expressing the translation product of a mycobacterial Ag85A (Ag85A) gene; and (b) at least one further antigen and/or microbial, in the manufacture of a medicament for administration to a human patient to induce a T cell immune response.

The vectored vaccine comprising a non-replicating or replication impaired viral vector expressing the translation product of a mycobacterial Ag 85A (Ag85A) gene and the further antigen(s) and/or antimicrobial(s) may be administered simultaneously, sequentially or separately. For example, the vectored vaccine may be administered to prime the patient before administration of the antigen(s)/antimicrobial(s) or after the administration of the antigen(s) to boost the patient's immune response to that antigen. The vectored vaccine and antigen(s)/antimicrobial(s) are preferably administered in admixture.

The invention also provides the use of at least one antigen and/or antimicrobial in the manufacture of a medicament for inducing a T cell immune response in a patient, wherein the medicament is administered with a vectored vaccine comprising a non-replicating or replication impaired viral vector expressing the translation product of a mycobacterial Ag85a (Ag85A) gene. Similarly, the invention provides the use of a vectored vaccine comprising a non-replicating or replication impaired viral vector expressing the translation product of a mycobacterial Ag 85A (Ag85A) gene in the manufacture of a medicament for inducing a T cell immune response in a patient, wherein the medicament is administered with at least one further antigen and/or antimicrobial.

The invention also provides the use of at least one antigen and/or antimicrobial in the manufacture of a medicament for inducing a T cell immune response in a patient, where the patient has been pre-treated with a vectored vaccine comprising a non-replicating or replication impaired viral vector expressing the translation product of a mycobacterial Ag85A gene. The invention also provides the use of a vectored vaccine comprising a non-replicating or replication impaired viral vector expressing the translation product of a mycobacterial Ag85A gene in the manufacture of a medicament for inducing a T cell immune response in a patient, where the patient has been pre-treated with at least one antigen and/or antimicrobial.

The present invention may be used to induce or enhance a variety of immune responses, as described above. In particular, it is an aim of this invention to identify an effective means of immunizing against diseases in which mycobacteria are implicated. Such diseases include Hansen's Disease, tuberculosis, osteomyelitis, Crohn's Disease, leprosy, lymphadenitis, Johne's disease.

The above-described aspects of the invention are applicable to a variety of different patients, including for example, children, patients who have HIV, AIDS, are immunocompromised/immunosupressed, or who have undergone organ transplants, bone marrow transplants or who suffer from genetic immunodeficiencies. Where the vaccine is for prophylactic use, the patient may be a child (e.g. an infant or child between 1-5 years), an older child or a teenager; where the vaccine is for therapeutic use, the patient is preferably an adult. A vaccine intended for children may also be administered to adults e.g. to assess safety, dosage, immunogenicity, etc.

The invention also provides a pharmaceutical composition comprising (1) an immunogenic composition of the invention and (2) a pharmaceutically acceptable carrier.

The invention provides a method of preparing a pharmaceutical, comprising the steps of: (i) preparing a vectored vaccine of the invention; and (ii) admixing the immunogenic composition with one or more pharmaceutically-acceptable carriers.

Carrier (2) can be any substance that does not itself induce the production of antibodies harmful to the patient receiving the composition, and which can be administered without undue toxicity. Suitable carriers can be large, slowly metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Stabilizing agents such as trehalose or substances that allow water-soluble sugar glass formation at ambient temperatures may also be present. The latter includes the use of mixed soluble glass stabilisation technology in microsphere format suspended in perfluorocarbon liquids. Liposomes are also suitable carriers. A thorough discussion of pharmaceutical carriers is available in Gennaro (2000) Remington: The Science and Practice of Pharmacy. 20th ed., ISBN: 0683306472.

Pharmaceutical compositions of the invention may also be used prophylactically e.g. in a situation where contact with microbes is expected and where establishment of infection is to be prevented. For instance, the composition may be administered prior to surgery.

The pharmaceutical composition is preferably sterile. It is preferably pyrogen-free. It is preferably buffered e.g. at between pH 6 and pH 8, generally around pH 7. Preferably, the composition is substantially isotonic with humans.

The compositions of the invention may be administered via a variety of different routes. Certain routes may be favoured for certain compositions, as resulting in the generation of a more effective response, or as being less likely to induce side effects, or as being easier for administration.

For example, the compositions utilised in this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means. The compositions may be prepared for intranasal administration, as nasal spray, nasal drops, gel or powder, as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, intranasally, or delivered to the interstitial space of a tissue. Dosage treatment may be a single dose schedule or a multiple dose schedule.

Various aspects and embodiments of the present invention will now be described in more detail by way of example, with reference to the following figures:

EXAMPLES

Example 1

The MVA85A Vaccine

Figure 1:
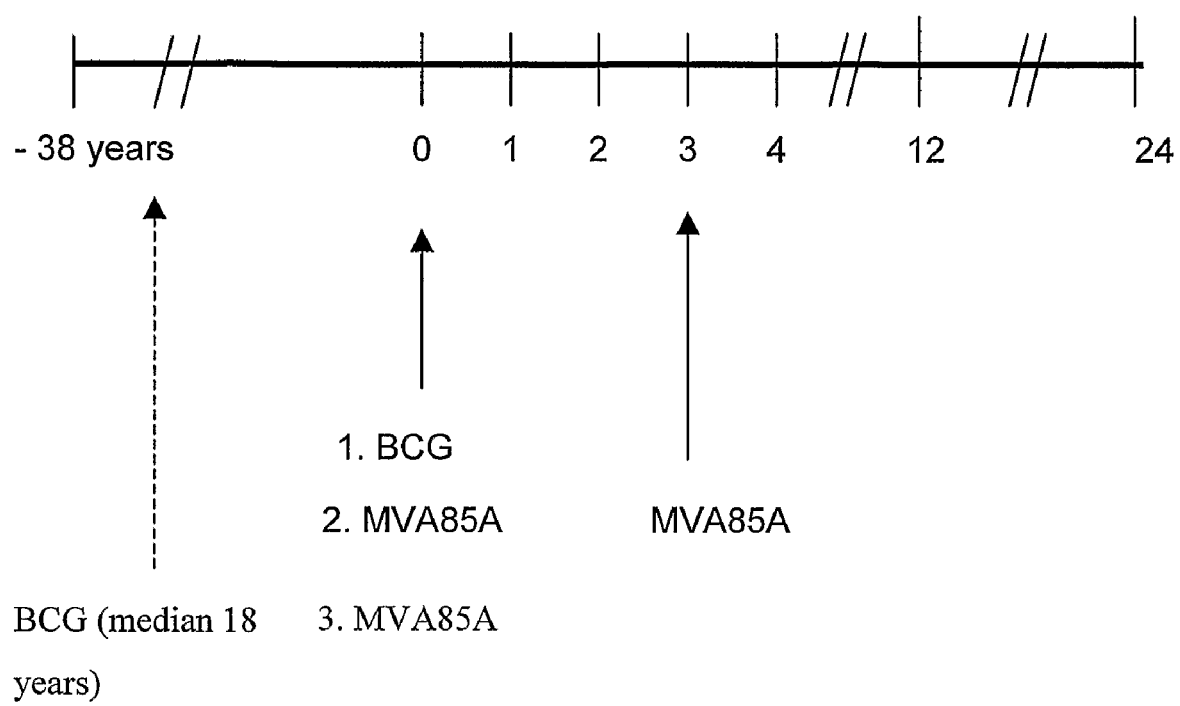
FIG. 1: Median IFN-γ ELISPOT responses after vaccination in each vaccination group: BCG alone; MVA85A alone; BCG prime-MVA85A boost. (a) timeline for vaccinations (weeks) in each group; (b) Tuberculin purified protein derivative (PPD) responses; (c) Purified antigen 85 (Ag85A) protein responses (d) summed pooled peptide responses; (e) For each of the three antigens measured, the responses between each vaccine group at each time-point were compared using Mann-Whitney statistic. Statistically significant comparisons are indicated; (f) T cell epitope display after MVA boost in BCG vaccinated individuals. All individual peptide responses were completely abrogated by CD4+ T cell depletion.

The construction of MVA85A has previously been described (McShane, H. et al. (2002) Infect. Immun. 70, 1623-1626). Clinical grade MVA85A was produced to good manufacturing practice standard by Impfstoffwerke Dessau-Tornau. A Doctors and Dentists Exemption Certificate was issued from the Medicines and Healthcare products Regulatory Agency, London, for the use of MVA85A in clinical trials.

Clinical Trials

Volunteers were recruited for immunisation studies under protocols approved by the Oxfordshire Research Ethics Committee and enrolled only after obtaining written informed consent. The age range for inclusion was 18-55 and all volunteers tested seronegative for HIV, HBV and HCV at screening. Routine laboratory haematology and biochemistry were performed prior to vaccination and all values were within normal limits. All volunteers were followed-up for 6 months, with blood samples taken at regular time points. Those who received MVA85A immunizations completed a diary card recording local and systemic side effects and body temperature for 7 days following vaccination.

Vaccinations

The first two studies were conducted in BCG naive healthy volunteers as determined using the Heaf test. The Heaf test involves placing tuberculin purified protein derivative (PPD) on the skin and then using a gun to produce multiple punctures. A positive reaction is more than 4 papules at the puncture sites at 72 hours. A positive skin test is indicative of active tuberculosis infection or previous BCG vaccination. Volunteers with a negative (Grade 0) Heaf test (equivalent to a tuberculin skin test of 0 mm) were vaccinated with either BCG (a single immunisation with BCG Glaxo strain, 100 µl administered intra-dermally, n=11) or MVA85A ($5 \times 10^7$ pfu administered intradermally, 2 immunizations given 3 weeks apart, n=14). In the third study, volunteers who had previously been vaccinated with BCG were recruited (n=17). The median time between BCG vaccination and immunization with MVA85A was 18 years (range 0.5-38 years). Volunteers with a Heaf test not greater than grade II (equivalent to a tuberculin skin test of <15 mm) in strength were enrolled in the study and immunized with a single dose of $5 \times 10^7$ pfu MVA85A intradermally into the skin overlying the deltoid on the contralateral arm to BCG vaccination. In total, 31 healthy volunteers were vaccinated with MVA85A. 11 of the 14 BCG naive volunteers received 2 immunizations, given 3 weeks apart. The remaining 3 received a single immunization. All of the 17 BCG-primed volunteers received a single MVA85A immunization. All volunteers completed the 6-month follow-up period and there were no serious or severe adverse events in any of these studies.

Immunogenicity Measures

The main immunological measure used to determine vaccine immunogenicity was the ex vivo IFN-γ ELISPOT assay. This was performed on blood taken at the following time points: at screening prior to the tuberculin skin test, and then at 1, 4, 12 and 24 weeks after vaccination. These measurements were carried out on fresh PBMCs using tuberculin PPD (20 µg/ml, SSI), purified antigen 85 (Ag85A) complex (10 µg/ml), and 7 pools of 9-10 15-mer peptides, overlapping by 10 amino-acids (10 µg/ml final concentration of each peptide in ELISPOT well.) Briefly, 300,000 PBMCs per well in 100 µl R10 (RPMI plus 10% foetal calf serum) were plated directly onto the ELISPOT plate (MAIP S4510, Millipore) in the presence of antigen, and incubated for 18 hours. Streptokinase (250 U/ml)/Streptodornase (12.5 U/ml) and phytohaemagglutinin (10 µg/ml) were used in all assays as positive controls. Assays were performed in duplicate and the results were averaged.

Epitope Mapping

Responses to individual peptides were either tested for on the first or subsequent sample after vaccination. Magnetic bead depletions (Dynal) were performed on individual peptide responses. CD4+ and CD8+ T cell depletions were performed by 30 minute incubation with monoclonal antibodies to CD4 and CD8 conjugated to ferrous beads at a ratio of 5 beads: 1 cell using M-450 (Dynal, Oslo, Norway) in 200 µl R10 on ice. Antibody coated cells were removed using a magnet (Dynal). Samples were analysed according to undepleted, CD4+ depleted and CD8+ T cell depleted groups. Cell depletions were confirmed by FACS scanning and were always >90% for CD8+ T cells and >97% for CD4+ T cells (data not shown).

Analysis of Immunogenicity

The ELISPOT data were analysed by subtracting the mean number of spots in the medium and cells alone control wells from the mean counts of spots in wells with antigens or peptide pools, and cells. Counts less than 5 spots/well were disregarded. A well was considered positive if the count was at least twice that in the negative control wells and at least 5 spots more than the negative control wells. For the peptide pool wells, the results were summed across all the peptide pools for each volunteer at each time point. For example, where there are 7 peptide pools, each containing 9-10 peptides, each pool is tested in duplicate. The mean of this duplicate for each pool is calculated, and the mean of the negative control well is subtracted, to give the result for that pool. The results for the 7 individual pools are then added together. This will potentially count twice a T cell that responds to any of the 10-mer overlap regions that occur in two pools with adjacent peptides.

Statistical Analysis

Analysis of variance for repeated measurements using the baseline result at screening as a covariate was performed on log transformed data to compare between groups. A Mann-Whitney test was then used for all comparisons between groups and a Wilcoxon test used for the paired comparison of screening and 24 week samples in the BCG prime-MVA85A boost group.

Cultured ELISPOT Method

For cultured ELISPOT, $1 \times 10^6$ cryopreserved PBMC were stimulated with 20 µg/ml of M.tb PPD ("PPD-T"), *M. avium* PPD ("PPD-A") or 10 µg/ml recombinant antigen 85A (Ag85A) in a 24-well plate. After a 3-day incubation period at +37° C. 5% $CO_2$ atmosphere 500 ul of the cell culture supernatant was removed and replaced with 5 IU/ml Lymphocult-T (Biotest, Dreieich, Germany) in R10. This was repeated on day 7. On day 9 the cells were washed three times and left to rest overnight in +37° C. 5% $CO_2$ atmosphere in R10. On day 10, cells were washed and resuspended in 2 ml of R10, 50 µl of cultured cells ($2.5 \times 10^4$ of the initially plated cells) were transferred to duplicate wells of an ELISPOT plate and stimulated for 18 hours with PPD-T 20 µg/ml, PPD-A 20 µg/ml and Ag85A 10 µg/ml. The ELISPOT plate was then developed as previously described.

Results

Immunization with MVA85A was safe and well tolerated (Table 1). The kinetics and magnitude of the antigen specific T cell response induced by vaccination with BCG alone, MVA85A alone and BCG prime-MVA85A boost were compared. All three vaccination regimes induce significant immune responses using either PPD-T, antigen 85 (Ag85A) protein or overlapping peptides from antigen 85A (Ag85A) as antigen in the assays (Table 2, FIG. 1). There was a significant main effect of vaccine in the PPD-T (F=3.624; P=0.037), antigen 85 (Ag85A) (F=16.605; P<0.001) and summed pooled antigen 85A (Ag85A) peptide group (F=39.982; P<0.001). Immunization with BCG induced moderate levels of antigen-specific IFN-γ secreting T cells, which peaked 4 weeks after immunization (Table 2, FIGS. 1*b-d*). Responses to the pooled antigen 85A (Ag85A) peptides were strikingly weak following BCG vaccination (FIG. 1*d*). Only 4 of the 11 volunteers responded to any of the 7 peptide pools in the ex-vivo ELISPOT assay. These peptide pool responses were all attributable to peptides 12, 13, 27 and 28, and were completely abrogated by CD4+ T cell depletion.

TABLE 1

Solicited adverse events after immunisation with MVA85A
There were no differences in either the frequency or severity of adverse
events reported between the BCG naïve and BCG primed groups

| | Adverse event | No. of subjects (n = 31) |
|---|---|---|
| Local | Redness | 31 |
| | Pruritus | 31 |
| | Pain | 30 |
| | Induration | 31 |
| Systemic[a] | Fever[b] | 5 |
| | Flu-like | 11 |
| | Arthralgia | 10 |
| | Headache | 11 |
| | Myalgia | 12 |
| | Nausea | 3 |
| | Vaso-vagal syncope | 1 (previous history of vaso-vagal attacks) |
| | Alterations in hematology/biochemistry | 0 |

Figure 1B:
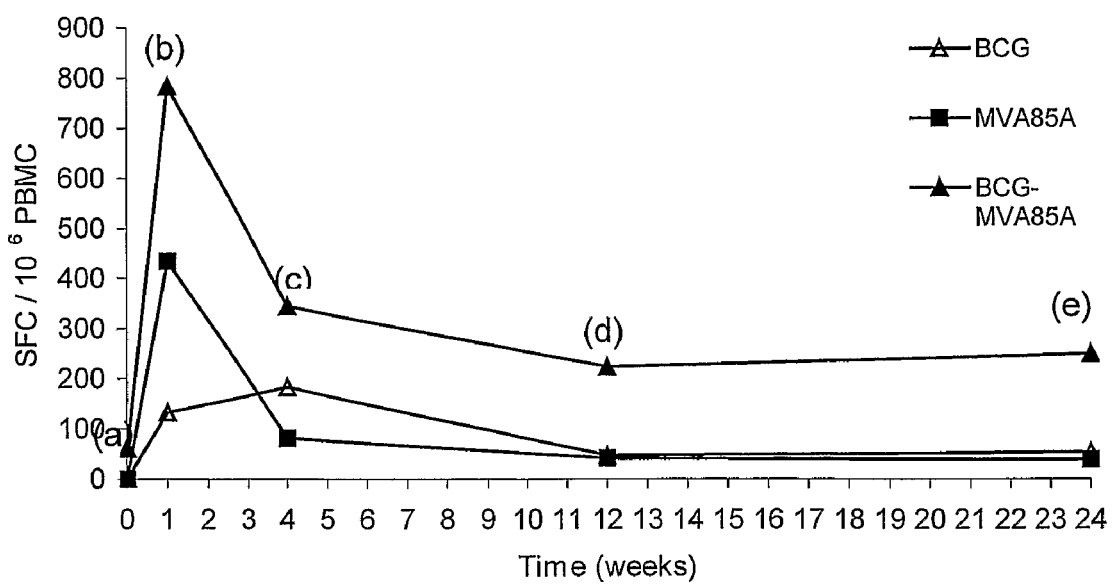
Figure 1:
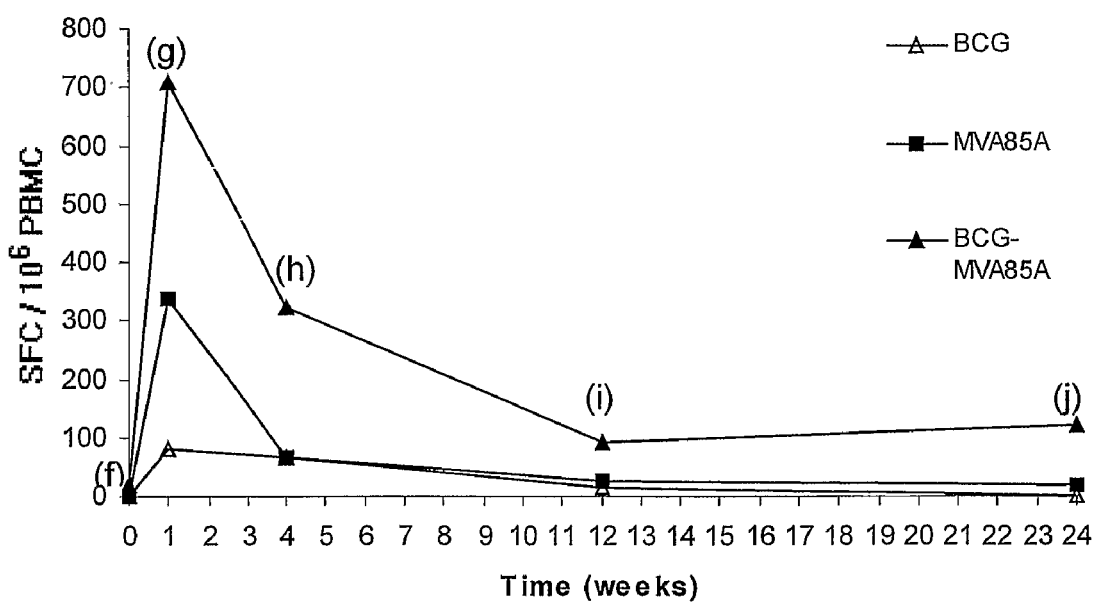

[a]All systemic symptoms resolved within 7 d
[b]Range 37.7-38.1° C.; all resolved spontaneously within 24 h In BCG naive volunteers, a single immunization with MVA85A induced high levels of antigen-specific IFN-γ secreting T cells which peaked 7 days after vaccination in 13/14 volunteers (Table 2, FIGS. 1b-c). By 4 weeks this response had fallen to a level just above baseline. No boosting effect of the second vaccination with MVA85A, administered at week 3, was seen. One volunteer did not develop insert-specific T cells following immunization with MVA85A, however this volunteer did develop specific T cell responses to the MVA vector, despite having no previous history of vaccinia immunization (data not shown). Responses to MVA-lac-Z in volunteers vaccinated with MVA85A was further investigated by performing ex vivo ELISPOT assays using MVA-lac-Z antigen. Assay methodology is as discussed above in "Immunogenicity measures". Healthy volunteers vaccinated with MVA85A demonstrated strong anti-MVA T cell responses which last for up to 24 weeks after vaccination.

In contrast to BCG vaccination, vaccination with MVA85A induced strong responses to several peptide pools in all of the 13/14 responding volunteers (Table 2, FIG. 1d). Responses were seen to a broad range of peptides across the whole length of antigen 85A (Ag85A). These individual peptide responses were all completely abrogated by CD4+ T cell depletion (data not shown).

In 16/17 volunteers in the BCG prime-MVA85A boost group, a significant rise in antigen specific T cells were seen 1 week after vaccination (Table 2, FIG. 1). The peak response 1 week after immunization was significantly higher in the BCG prime-MVA85A boost group than in either the BCG or MVA85A alone groups, (FIGS. 1b-e). These responses were sustained at a significantly higher level than after vaccination with either BCG or MVA85A alone, for at least 24 weeks (FIG. 1e). The baseline responses at screening were higher in the volunteers previously vaccinated with BCG, than in the BCG naïve group, as would be expected. Nonetheless, the responses 24 weeks after vaccination with MVA85A in the BCG prime-MVA85A boost group were significantly higher than baseline counts in this group for PPD (Wilcoxon z=−3.010, P=0.003), Antigen 85 (Ag85A) (Wilcoxon z=−3.516, P <0.001) and the summed pooled peptides (Wilcoxon z=−3.408, P=0.001).

Figure 1F:
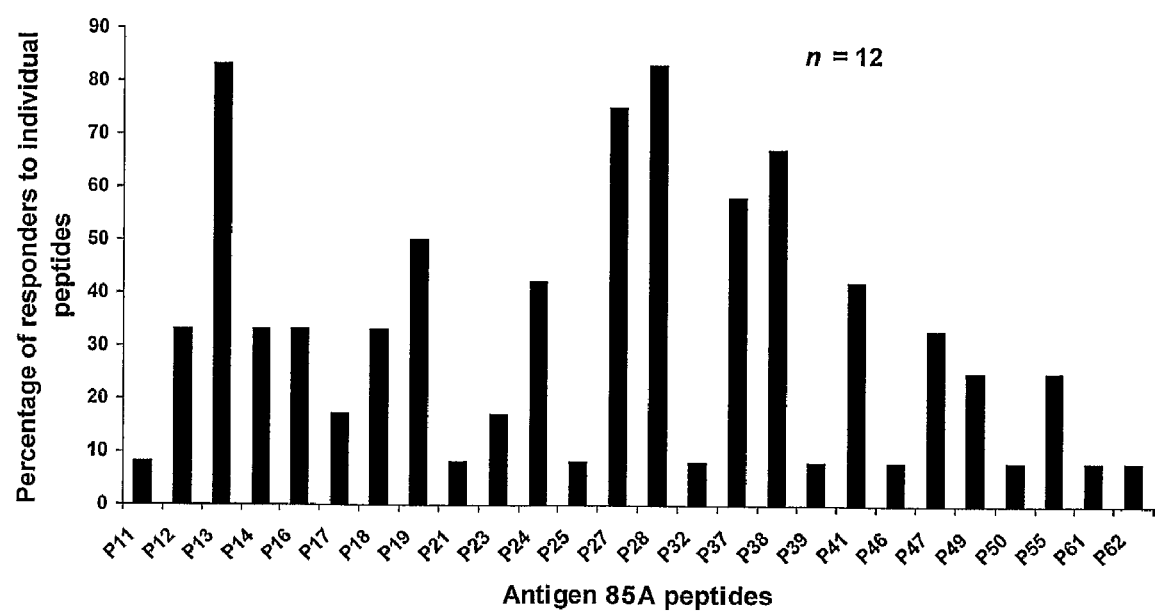

The breadth of peptide responses seen in the MVA85A alone (not shown) and BCG prime-MVA85A boost groups (FIG. 1f) were very similar. However, the magnitude of responses was significantly higher in the BCG prime-MVA85A boost group (FIG. 1e). PBMC from 12 volunteers in the BCG prime-MVA85A boost group were assayed with all 66 peptides from antigen 85A (Ag85A). Several of these peptides were recognized by more than 50% of subjects (FIG. 1f), illustrating the promiscuous recognition of these peptides by different HLA Class II molecules, as previously reported (Launois, P. et al. (1994) Infect. Immun. 62, 3679-3687.

TABLE 2

Arithmetic mean (SE) and median (IQR) ELISPOT responses to PPD, antigen 85 (Ag85A) and summed pooled peptides in each vaccination group at each time point.

| Time after vaccination (weeks) | Vaccine group | Number | PPD arithmetic mean (SE) | median (25-75%) | Antigen 85 arithmetic mean (SE) | median (25-75%) | Summed pooled peptides arithmetic mean (SE) | median (25-75%) |
|---|---|---|---|---|---|---|---|---|
| 0 | BCG | 11 | 15 (6) | 0 (0-28) | 6 (5) | 0 (0-0) | 15 (4) | 20 (0-22) |
| | MVA85A | 14 | 18 (7) | 0 (0-22) | 4 (4) | 0 (0-0) | 3 (3) | 0 (0-0) |
| | BCG-MVA85A | 17 | 129 (33) | 60 (28-218) | 24 (6) | 18 (0-37) | 26 (11) | 0 (0-50) |
| 1 | BCG | 11 | 173 (52) | 132 (42-249) | 79 (22) | 82 (23-122) | 38 (9) | 28 (20-52) |
| | MVA85A | 14 | 460 (93) | 434 (175-553) | 419 (98) | 338 (140-540) | 1365 (378) | 1153 (531-1432) |
| | BCG-MVA85A | 17 | 917 (148) | 783 (403-1653) | 895 (150) | 707 (438-1653) | 3248 (592) | 2455 (1315-5187) |
| 4 | BCG | 11 | 233 (50) | 182 (104-314) | 64 (12) | 67 (37-94) | 31 (7) | 35 (13-40) |
| | MVA85A | 14 | 107 (21) | 81 (53-167) | 117 (42) | 65 (33-138) | 306 (95) | 156 (60-533) |
| | BCG-MVA85A | 17 | 362 (86) | 343 (165-421) | 341 (67) | 322 (180-405) | 1123 (266) | 953 (609-1219) |
| 12 | BCG | 11 | 76 (25) | 47 (27-85) | 21 (8) | 15 (0-33) | 15 (9) | 0 (0-17) |
| | MVA85A | 14 | 70 (25) | 41 (22-92) | 59 (26) | 27 (18-52) | 167 (58) | 68 (21-205) |
| | BCG-MVA85A | 17 | 299 (83) | 223 (68-387) | 227 (72) | 92 (42-287) | 739 (199) | 390 (212-910) |
| 24 | BCG | 11 | 58 ((17) | 53 (10-95) | 12 (6) | 0 (0-22) | 23 (7) | 20 (0-35) |
| | MVA85A | 14 | 62 (19) | 38 (26-63) | 32 (13) | 18 (0-45) | 113 (27) | 105 (32-152) |
| | BCG-MVA85A | 16 | 328 (89) | 249 (150-385) | 240 (77) | 119 (82-293) | 669 (177) | 385 (223-1043) |

The magnitude of T cell responses seen in the MVA85A alone group are stronger by a factor of about 10 than those seen with other recombinant MVAs used to date (McConkey, S. J. et al., "Enhanced T-cell immunogenicity of plasmid DNA vaccines boosted by recombinant modified vaccinia virus Ankara in humans", Nat. Med., 9, 729-735 (2003)); Mwau, M. et al., "A human immunodeficiency virus 1 (HIV-1) clade A vaccine in clinical trials: stimulation of HIV-specific T-cell responses by DNA and recombinant modified vaccinia virus Ankara (MVA) vaccines in humans", J. Gen. Virol., 85, 911-919 (2004)). A recombinant MVA expressing an antigen from *P. falciparum* induced a mean summed peptide response of 90 SFC/106 PBMC 7 days after vaccination (McConkey, S. J. et al. (2003) Nat. Med. 9, 729-735). In contrast, we see a mean response to the summed peptides of 1365 SFC/106 PBMC 7 days after vaccination with MvA85A (Table 2). One explanation for this is that these volunteers have some pre-existing anti-mycobacterial immunity, which is being boosted by immunization with MVA85A. We used a cultured, rather than an ex-vivo ELISPOT assay to investigate this further. The cultured ELISPOT assay has previously been shown to measure central memory type T cells, rather than the activated effector T cells that are measured by ex-vivo ELISPOT (Reece, W. H. et al. (2004) Nat. Med. 10, 406-410, Godkin, A. J. et al. (2002) J. Immunol. 169, 2210-2214).

Figure 2:
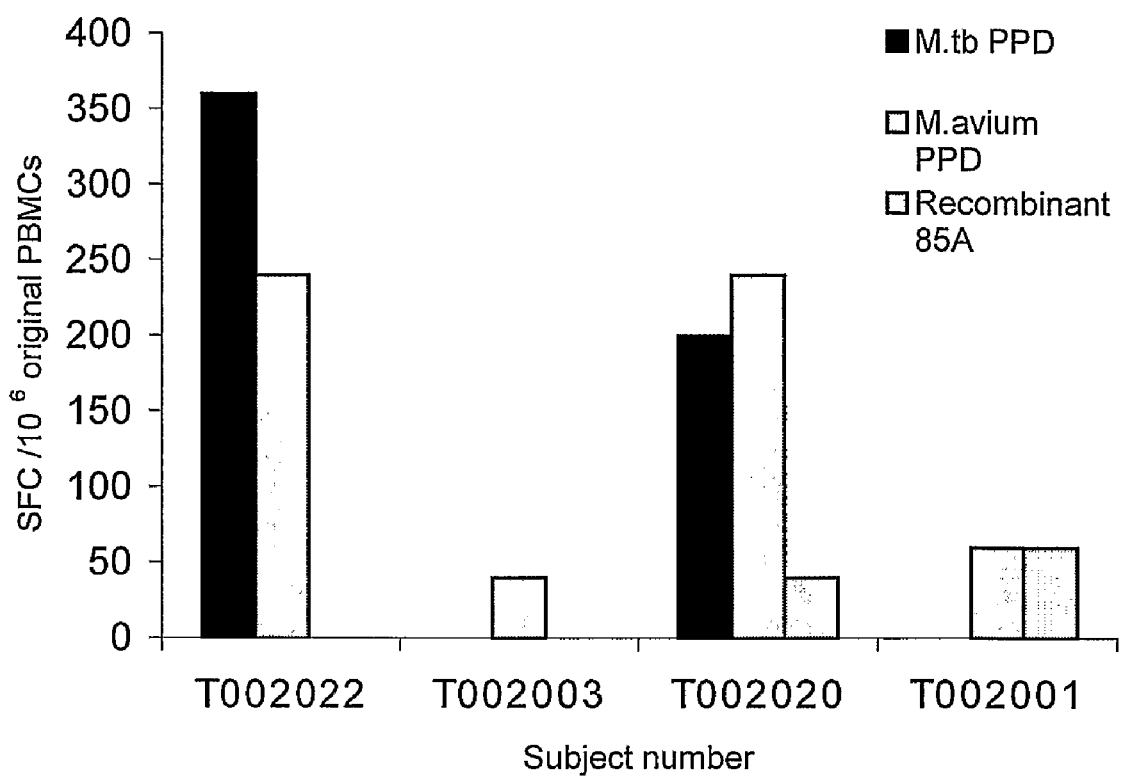
FIG. 2: Screening blood cultured ELISPOT responses to M.tb PPD; *M avium* PPD and recombinant antigen 85A (Ag85A); from 4 volunteers in the MVA85A alone study, prior to vaccination; Each volunteer is identified by a code TXXXXXX, where the first three Xs correspond to the trial number and the last three Xs correspond to the volunteer number, e.g., T002022 means that T002 is trial number and 022 is volunteer number.

A cultured IFN-γ ELISPOT assay was performed on the pre-vaccination screening PBMC from 4 of the volunteers in the MVA85A alone group. Cells were cultured with M.tb PPD, *M avium* PPD and recombinant antigen 85A (Ag85A). All 4 volunteers responded to *M. avium* PPD, 2/4 responded to M.tb PPD and 2/4 responded to recombinant antigen 85A (Ag85A) (FIG. 2). None of these volunteers had any baseline responses to either M.tb PPD or purified antigen 85 (Ag85A) on the screening ex-vivo ELISPOT.

Figure 3:
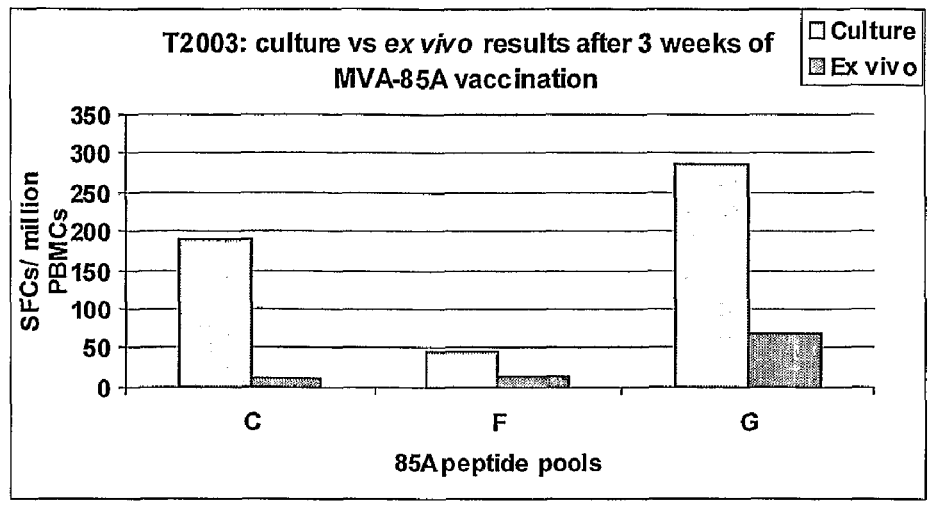
FIG. 3: Cultured (labelled "culture") and ex vivo ELISPOT responses to pools of Ag85A peptides (labelled with upper case letters) in five volunteers (each identified by a code TXXXX, where XXXX is a four digit number, digit one corresponding to trial number and digits two, three and four corresponding to volunteer number, e.g., T2003 means that T2 is trial number and 003 is volunteer number (T2 is the same as T002 in FIG. 2 above)) three weeks after administration of a single MVA85A immunization. Post-vaccination responses are very high and are higher than pre-vaccination responses. Volunteers were not previously vaccinated with BCG.
Figure 3:
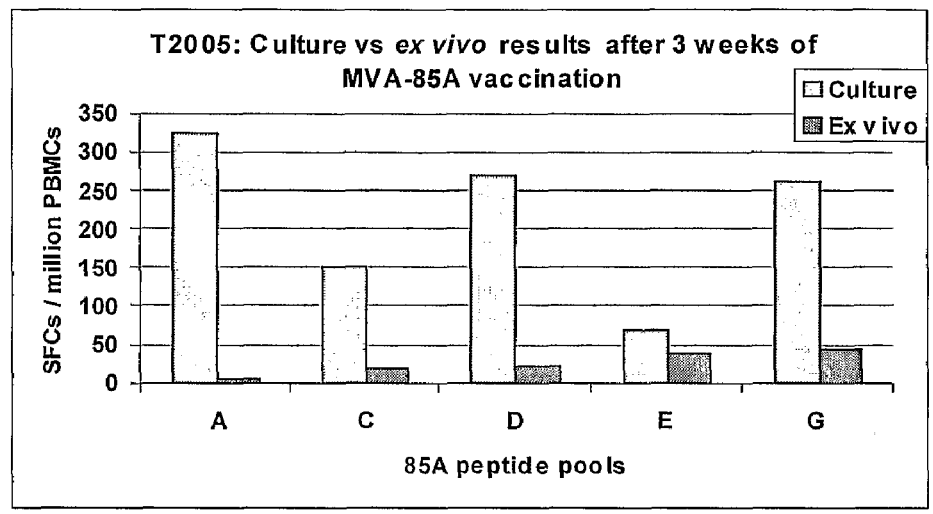
Figure 3:
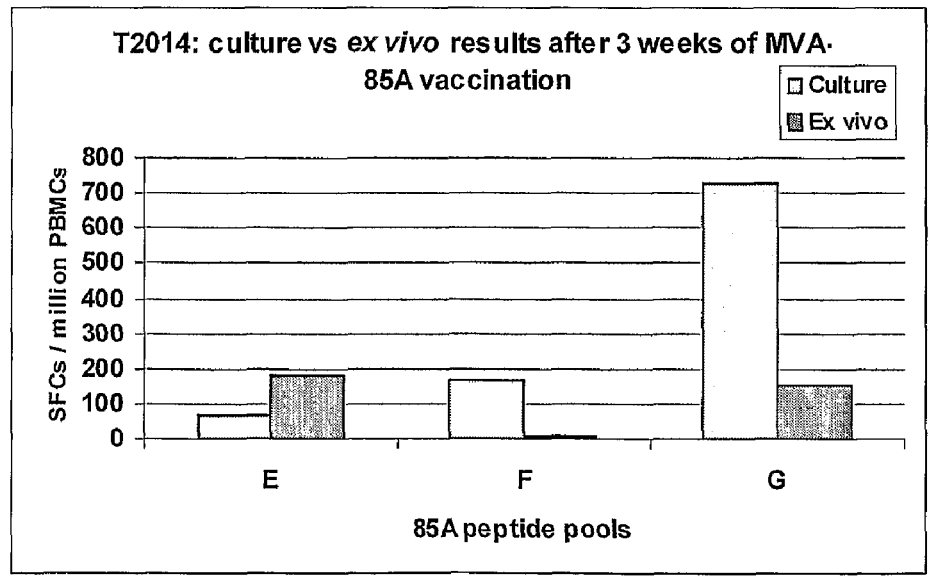
Figure 4:
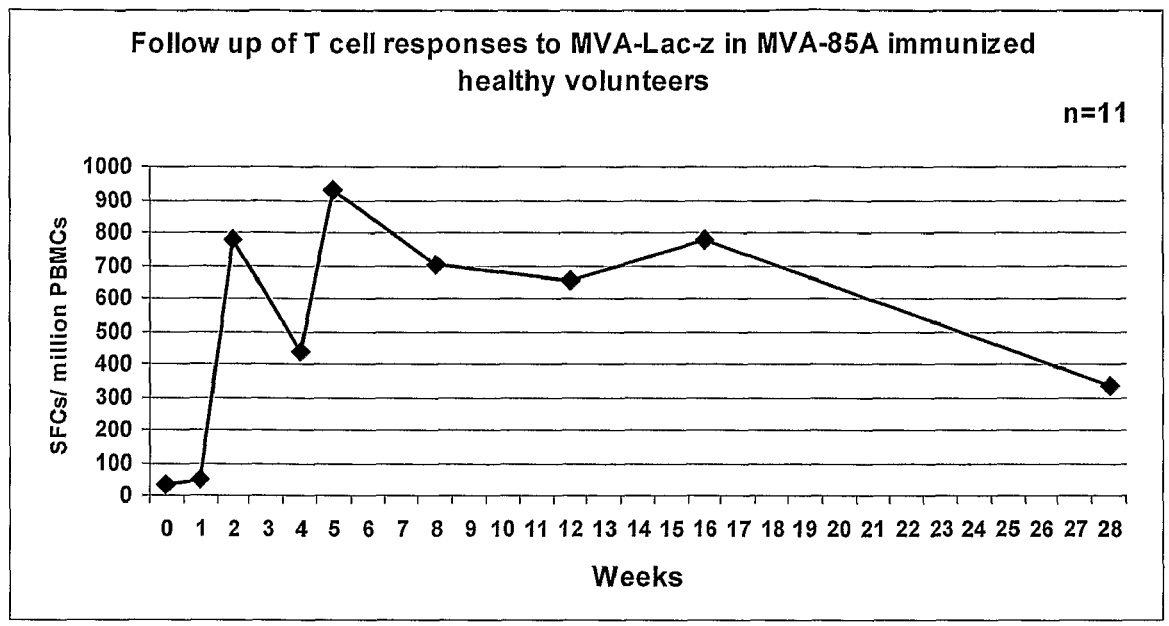
FIG. 4: Follow up of T cell responses to MVA-Lac-z used as the antigen in an ex vivo ELISPOT assay in MVA-85A immunized healthy volunteers immunised once at week 1. Volunteers had been previously vaccinated with BCG.

To further investigate the induction of a memory T cell response following vaccination with MVA85A, an ex vivo and a cultured ELISPOT assay was performed on the 3 week post vaccination PBMC. Cells were cultured with M.tb PPD, *M. avium* PPD and recombinant antigen 85A (Ag85A). At 3 weeks the ex-vivo response is very low or undetectable, however in all 5 volunteers tested there were strong responses on the cultured ELISPOT indicating the induction by vaccination of central memory T cells specific for antigen 85A (Ag85A) (FIG. 3).

Example 2

Figure 5A:
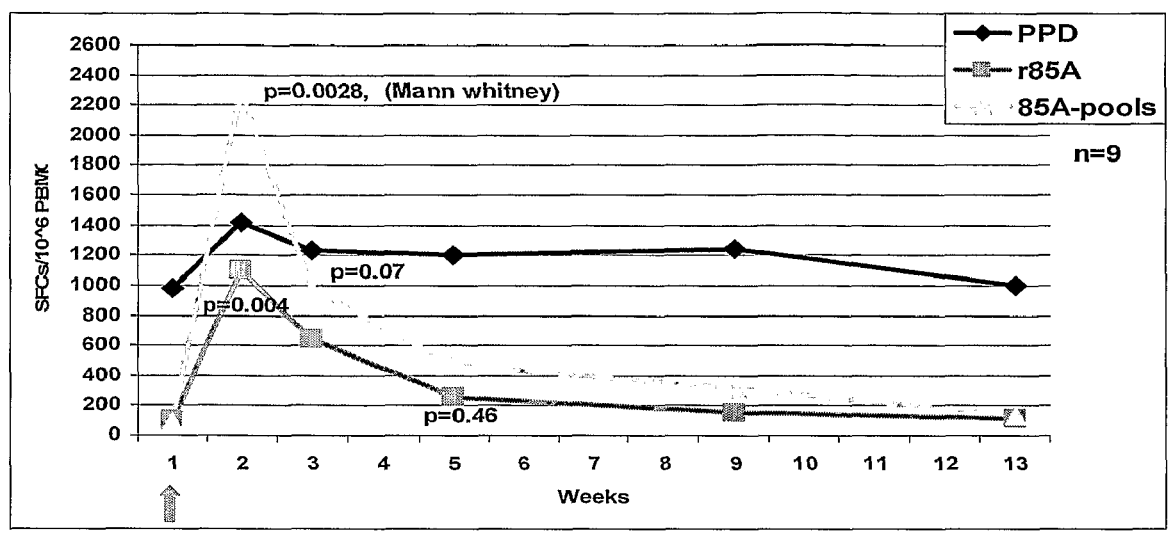
FIG. 5(a) Median Elispot responses to PPD, recombinant antigen 85A (Ag85A) and summed Antigen 85A (Ag85A) peptide pools after a single vaccination with MVA85A in subjects latently infected with M.tb.

Safety and Immunogenicity Data in Subjects who are Latently Infected with M.tb 9 healthy adults who were latently infected with *Mycobacterium tuberculosis* (M.tb) were vaccinated with MVA85A. Serum inflammatory markers were measured at regular intervals after vaccination in each subject over a period of twelve months. A high resolution CT scan of the lungs was performed in each subject before vaccination and 10 weeks after vaccination. These tests were performed in order to detect any subclinical signs of pulmonary inflammation. The results of the ex vivo Elispot results from the 9 latently infected volunteers are shown in FIG. 5a.

The safety of MVA85A in this group is identical to that seen in the previous trials described in Example 1. No increase in either local or systemic side effects was detected and neither were signs of any pulmonary inflammation detected. Inflammatory markers did not change after vaccination and there was no lung inflammation detectable by CT scan post vaccination.

Figure 5B:
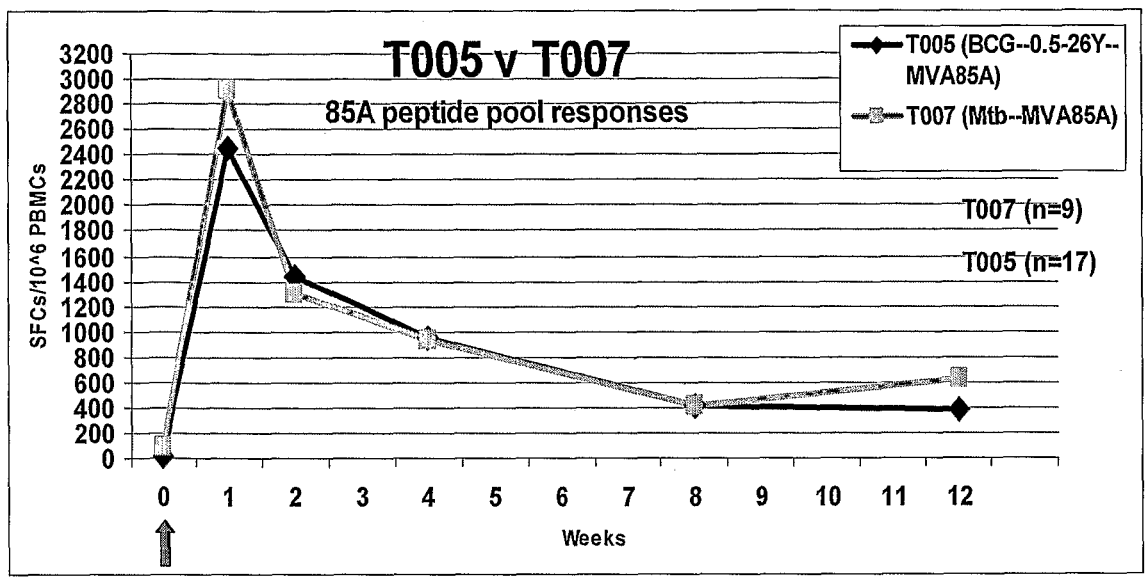
FIG. 5(b) Comparison of MVA85A induced summed Antigen 85A (Ag85A) pooled peptide responses in BCG primed subjects (T005, i.e., trial 5; see example 1) and M.tb latently infected subjects (T007, i.e., trial 7)
Figure 5C:
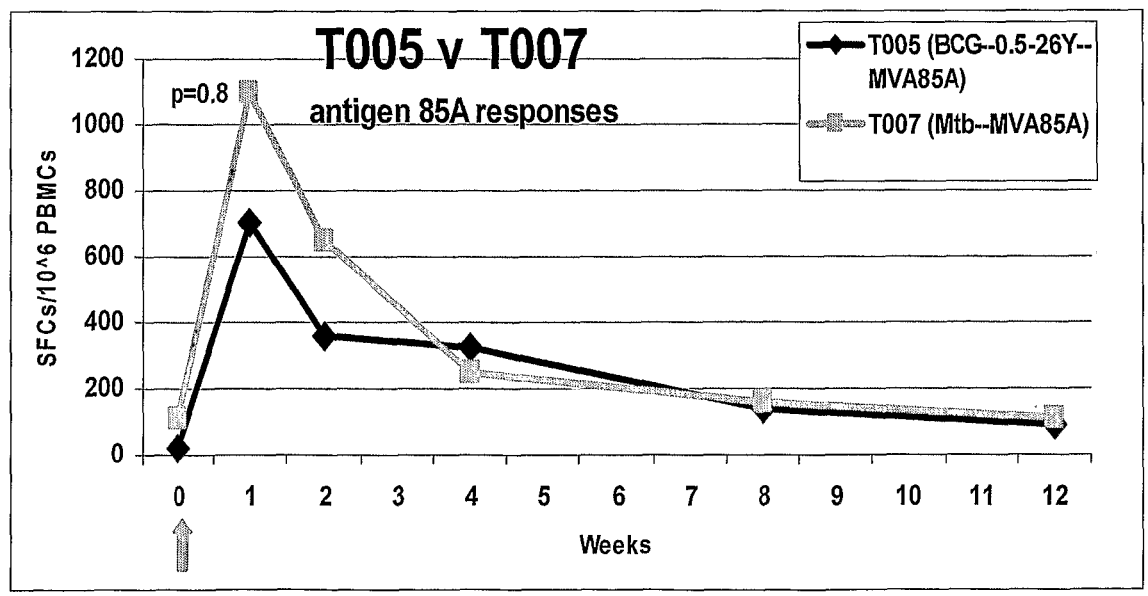
FIG. 5(c) Comparison of MVA85A induced recombinant Antigen 85A (Ag85A) responses in BCG primed subjects (T005) and M.tb latently infected subjects (T007)

As a comparison, 17 healthy adults who had previously received a BCG injection 0.5 to 37 years ago were boosted with the MVA85A vaccination. The results are described in Example 1. The immune responses post vaccination seen in the latently infected group (trial 7, "T007") are of a similar magnitude to that seen in the BCG primed group (trial 5, "T005"). The results are shown in FIGS. 5b and 5c.

This data is significant because it is important that any new TB vaccine is safe in latently infected subjects, given the prevalence of latent infection throughout the developing world. In addition, the encouraging immunogenicity supports the application of this vaccine as a post exposure vaccine, administered to latently infected people, with the aim of eradicating such latent infection.

Duration of Immune Response

Ex vivo ELISPOT responses in BCG primed volunteers after MVA85A boosting last for at least 1 year after vaccination, with both a short (1 month) and long (more than 10 years) interval between prime (BCG) and boost (MVA85A).

Figure 6A:
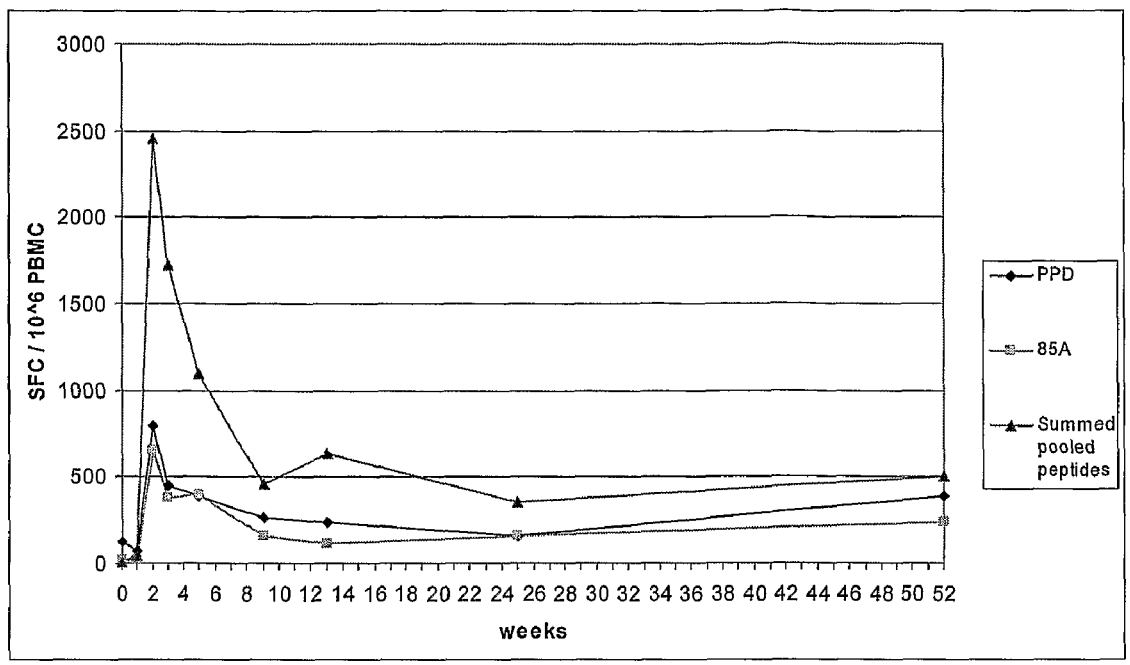
FIG. 6a: Persistence of the MVA85A induced immune responses for at least 1 year after vaccination in a subject group with a long (more than 10 years) interval between prime (BCG) and boost (MVA85A)
Figure 6B:
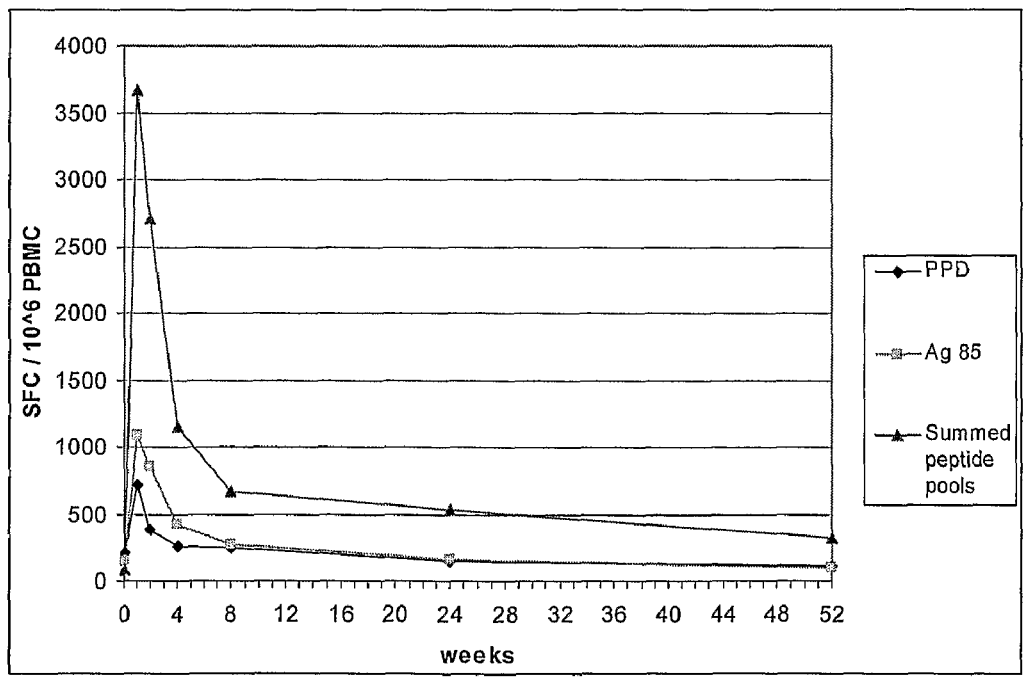
FIG. 6(b): Persistence of the MVA85A induced immune responses for at least 1 year after vaccination in a subject group with a short (1 month) interval between prime (BCG) and boost (MVA85A)

Long term follow up data on 12 volunteers vaccinated with MVA85A more than 10 years after BCG, and 10 volunteers vaccinated with MVA85A 1 month after BCG is shown in FIG. 6. The data from both sets of volunteers show persistence of immune responses at 1 year after vaccination is at the same magnitude as seen at 6 months after vaccination.

The persistence of vaccine induced immune responses demonstrates the induction of a memory response. One would not expect to see persistent vaccine induced responses 1 year after vaccination with a non-replicating vaccine, unless a memory response had been induced.

Correlation Between Prime-Boost Interval and Level of Immune Response

The data presented in FIG. 3 indicates that the boosting of BCG induced immune responses seen after MVA85A boosting vaccination does not depend on the interval between BCG priming and MVA85A boosting. Equal boosting was seen with a short (1 month) and a long (more than 10 years) boosting interval.

Figure 7A:
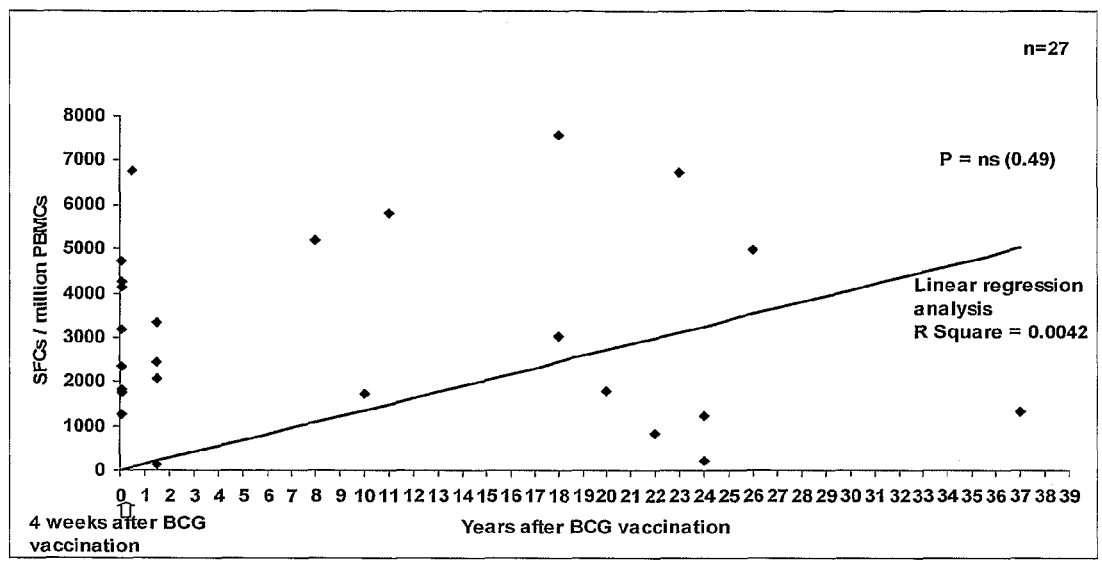
FIG. 7(a) Lack of correlation between interval between BCG and MVA85A vaccination and 1 week post MVA85A T cell responses to antigen 85A (Ag85A) summed peptide pools.
Figure 7B:
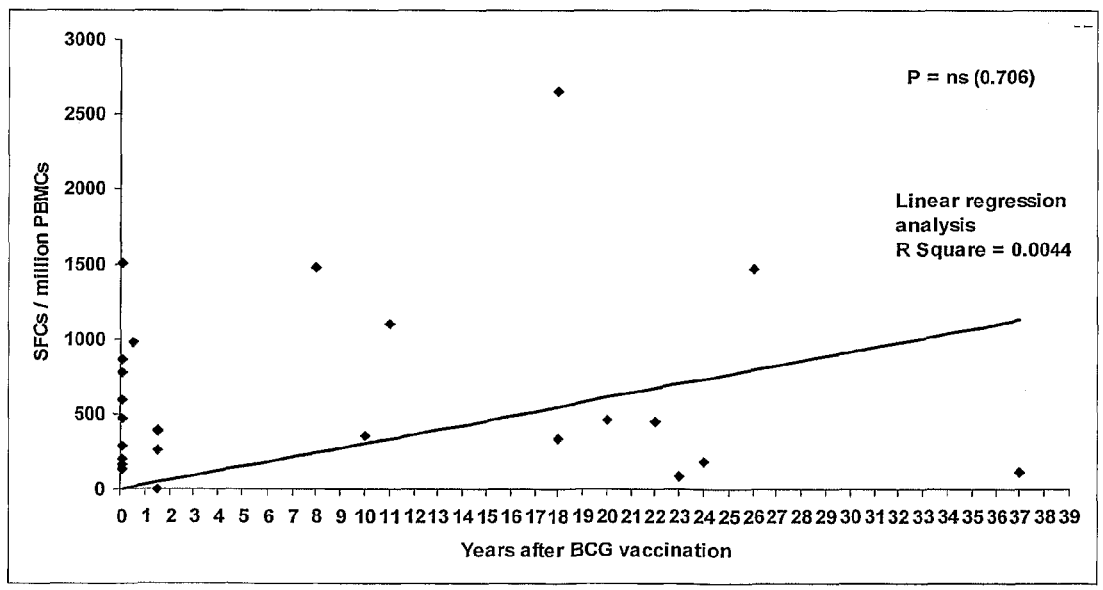
FIG. 7(b) Lack of correlation between interval between BCG and MVA85A vaccination and 24 weeks post MVA85A T cell responses to antigen 85A (Ag85A) summed peptide pools.

There is no correlation between the interval between prime (BCG) and boost (MVA85A) vaccination and either peak (1 week) or plateau (6 months) MVA85A induced immune responses (FIG. 7).

Thus boosting mycobacterial immunity either soon after BCG vaccination (e.g. in infancy in the developing world), or at a later time point (e.g. in adolescence), is equally feasible. Both boosting in infancy and boosting in adolescence are possible options for efficacy trials and potential indications for a booster TB vaccine.

Immunogenicity and Protective Efficacy of BCG Prime—MVA85A Boost in Rhesus Macaques In an immunogenicity and challenge experiment, rhesus macaques (6/group) were vaccinated with either i) BCG alone, ii) BCG and then boosted 9 weeks later with MVA85A, or iii) saline (control group). All animals were challenged intra-tracheally 18 weeks after the BCG vaccination (or saline vaccination for the control group) and then followed for 16 weeks before being euthanized. The immunogenicity results are shown in FIG. 8.

Figure 8A:
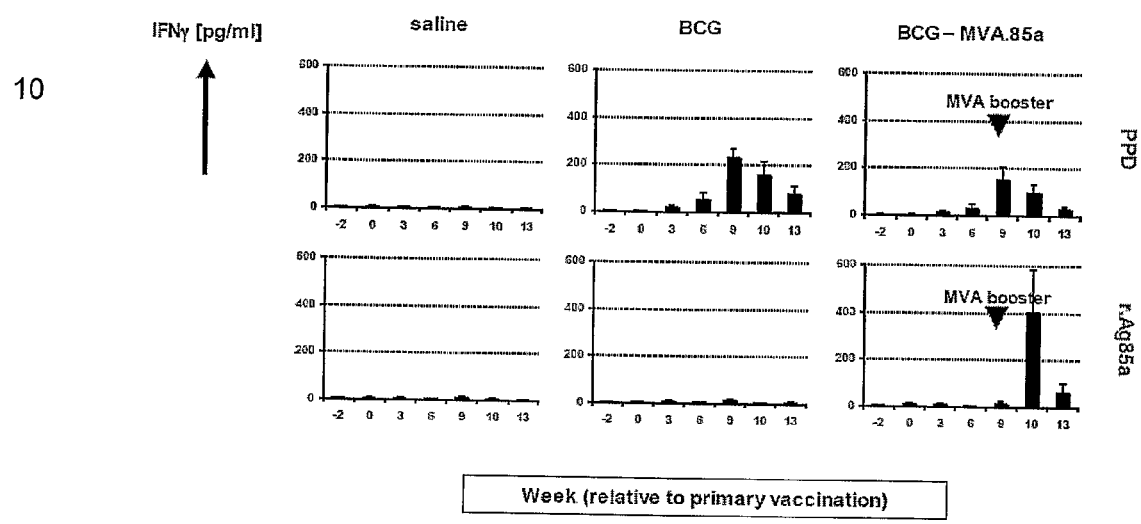
FIG. 8a shows mean levels of IFN-γ post vaccination.

FIG. 8a shows mean levels of IFN-γ post vaccination (as measured by a 3 day lymphocyte stimulation test) in all three groups within this challenge experiment. Whilst levels of IFNγ in response to PPD in the BCG and BCG prime-MVA85A group seem comparable, the responses to Ag85A are clearly higher in the BCG prime-MVA85A boost group. Thus, there is a significant rise in Ag85A-specific IFN-γ secretion after MVA85A vaccination (group ii) that is not seen in the BCG alone group (group i) (FIG. 8a).

Figure 8B:
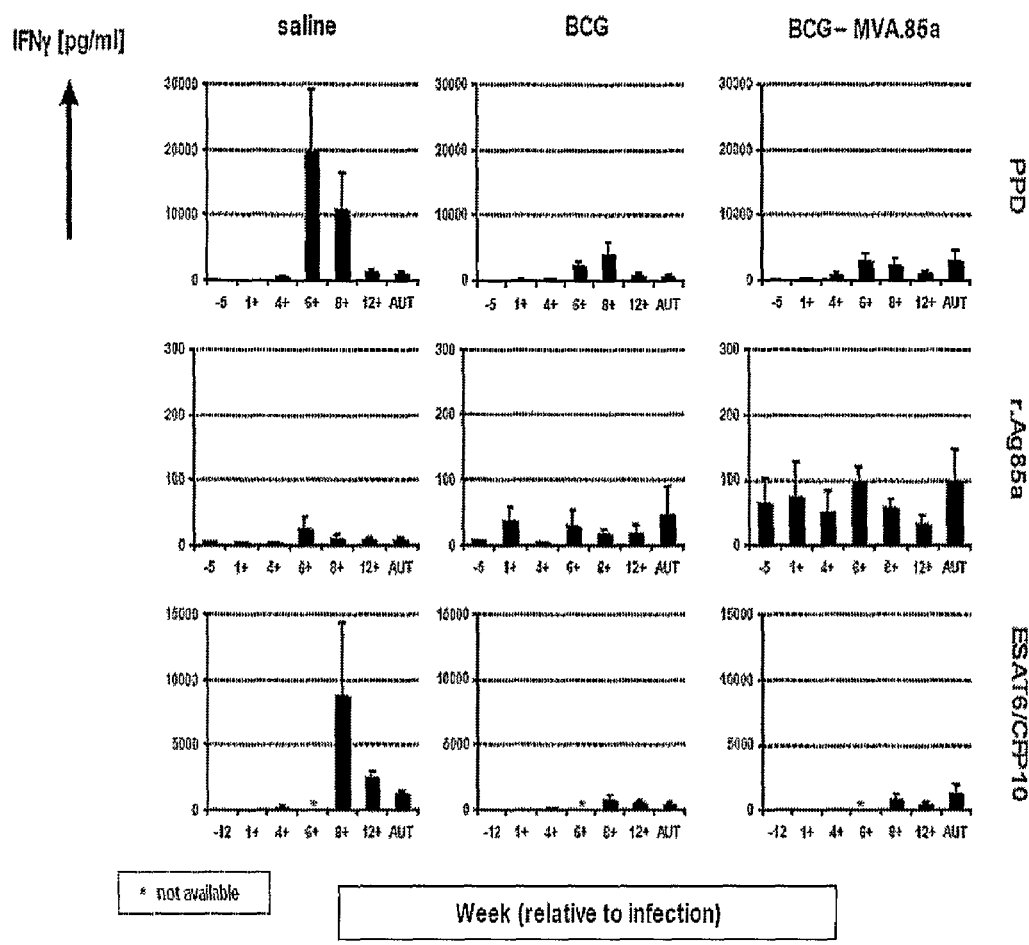
FIG. 8b shows mean levels of IFN-γ post challenge.

FIG. 8b shows mean levels of IFN-γ post challenge (as measured by a 3 day lymphocyte stimulation test) in all three groups within this challenge experiment. After challenge with M.tb, the BCG-MVA85A group (group ii) had significantly higher Ag85A-specific responses than the BCG alone group (group i). Also the ESAT6/CFP10 responses (early secreted antigenic target protein/culture filtrate protein 10), which are the M.tb-specific immune responses (the magnitude relates to bacterial load), are lower in the BCG and the BCG-MVA85A groups, compared with the saline group. The PPD responses are comparable between these two groups. The ESAT6/CFP10 results are important (lowest panel) as these antigens are TB specific and levels of immune responses to these antigens correlate with bacterial load (i.e., the higher the bacterial load (saline group), the higher the immune response to ESAT6 and CFP10). The protective efficacy of the vaccine is implied by the relatively lower level of the ESAT6/CFP10 response in the BCG and the BCG-MVA85A groups, compared with the saline group.

At autopsy, there was considerably less pathology seen in the BCG-MVA85A group than in the BCG alone group. The reduction in bacterial load in these 2 groups was 0.97 for the BCG-MVA85A group and 0.42 for the BCG alone group.

The rhesus macaque is a good model of human disease and this promising improvement in protective efficacy despite small numbers of animals suggests that similar efficacy results would be expected in humans.

Safety and Immunogenicity Data from Phase II Studies in Adults in South Africa

A Phase II safety and immunogenicity study has been commenced in the Western Cape, South Africa. This trial is in adults and the target is 24 subjects. Subjects who are latently infected are excluded from this study. To date, 12 subjects have been vaccinated. All 12 subjects had significant MVA85A-induced immune responses on their 1 week post vaccination Elispot assay.

Figure 9A:
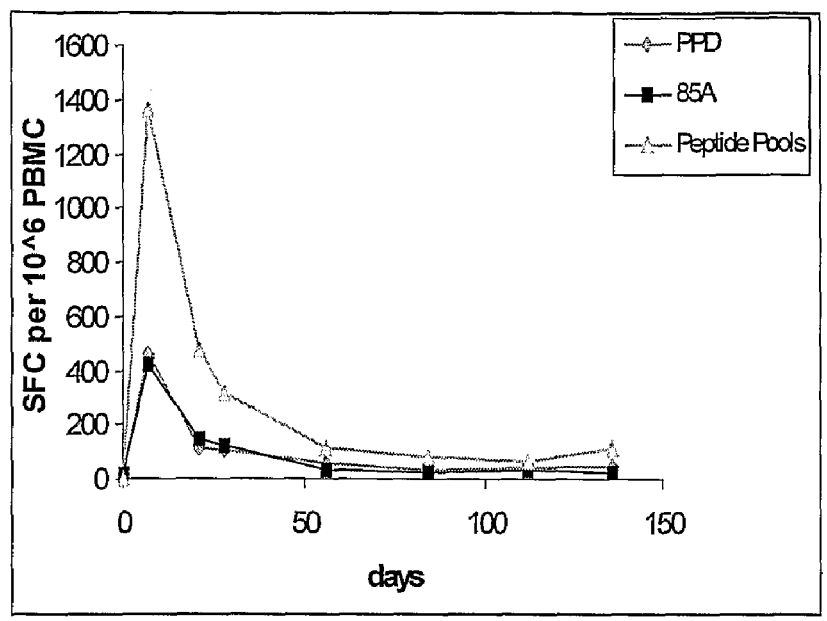
FIG. 9(a) shows ex-vivo IFN-γ Elispot responses to MVA85A in BCG naive UK volunteers.
Figure 9B:
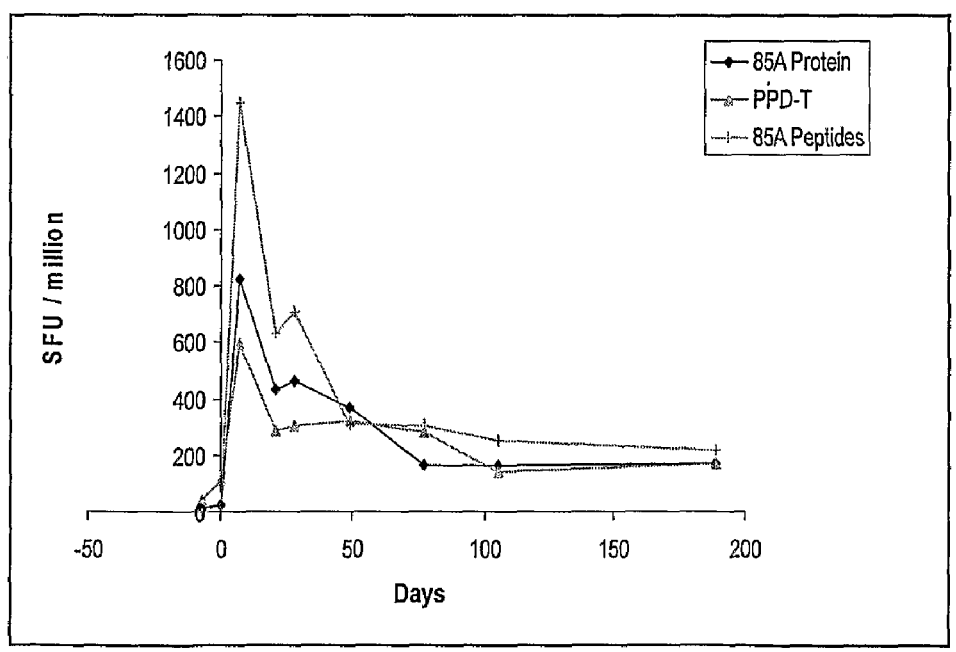
FIG. 9(b) shows ex-vivo IFN-γ Elispot responses to MVA85A in BCG naive Gambian volunteers.

The safety profile to date is the same as that seen in the UK and Gambia studies. The results of the UK studies are shown in FIG. 1 and FIG. 9a and the results of the Gambian study are shown in FIG. 9b.

In total, 11 BCG naïve volunteers and 10 BCG primed volunteers were vaccinated in the Gambia. The immunogenicity results of the BCG naïve group (FIG. 9b) resembled the immunogenicity results of the BCG primed group in the UK (FIGS. 1b, 1c, 1d), in that they remain above base line for the duration of follow-up. This is likely to reflect a greater degree of priming by environmental mycobacteria at baseline, and also ongoing exposure to environmental mycobacteria which is maintaining the response.

There is no significant difference between the BCG naïve and BCG primed groups in the Gambia, which is explained as above by the greater degree of environmental priming in this group. In contrast, in the UK, the immunogenicity results of the BCG naïve group returned to the base line during the follow-up (FIG. 9a and FIGS. 1b, 1c and 1d), whereas the BCG primed group remain above base line for the duration of follow-up (FIGS. 1b, 1c and 1d).

Throughout the BCG literature, there are many examples of wide variability in protective efficacy across different countries and continents. The consistent safety and immunogenicity profile of MVA85A in the UK, West Africa and South Africa is very significant.

Immunogenicity in Mice of Adenovirus Expressing Antigen 85A (Ag85A)

A recombinant adenovirus (human strain 5, E1 and E3 deleted) expressing antigen 85A (Ag85A) has been shown to induce strong immune responses in mice when given alone (CD4 response c 800 spots/million splenocytes; CD8 response c 1200 spots/million splenocytes). When administered to mice that have previously received BCG, this adenovirus expressing antigen 85A (Ag85A) stimulates an even stronger response (CD4 response c 1400 spots/million splenocytes; CD8 response c 2500 spots/million splenocytes). Thus this adenovirus vector, remarkably, is shown here to induce, in addition to very strong CD4, very strong CD8 T cell responses and the induction of these by the same vaccine is likely to be of benefit in both prophylaxis and treatment of mycobacterial disease. Previously adenovirus vectors have been seen as a good means of inducing CD8 T cell responses but here we show that both CD4 and CD8 responses are powerfully induced. This data suggests adenoviral vectors can be a powerful boost for BCG primed T cell responses.

The invention has been described above by way of example only. It will be appreciated that modification of detail may be made without departing from the scope of the invention.

```
AG85A SPECIFIC SEQUENCES
SEQ ID NO: 1
(AG85A POLYPEPTIDE SEQUENCE)
MQLVDRVRGAVTGMSRRLVVGAVGAALVSGLVGAVGGTATAGAFSRPGLP

VEYLQVPSPSMGRDIKVQFQSGGANSPALYLLDGLRAQDDFSGWDINTPA

FEWYDQSGLSVVMPVGGQSSFYSDWYQPACGKAGCQTYKWETFLTSELPG

WLQANRHVKPTGSAVVGLSMAASSALTLAIYHPQQFVYAGAMSGLLDPSQ

AMGPTLIGLAMGDAGGYKASDMWGPKEDPAWQRNDPLLNVGKLIANNTRV

WVYCGNGKPSDLGGNNLPAKFLEGFVRTSNIKFQDAYNAGGGHNGVFDFP

DSGTHSWEYWGAQLNAMKPDLQRALGATPNTGPAPQGA

SEQ ID NO 2
(AG85A NUCLEOTIDE SEQUENCE)
atgcagcttgttgacagggttcgtggcgccgtcacgggtatgtcgcgtcg actcgtggtcggggccgtcggcgcggccctagtgtcgggtctggtcggcg ccgtcggtggcacggcgaccgcggggcattttcccggccgggcttgccg gtggagtacctgcaggtgccgtcgccgtcgatgggccgtgacatcaaggt ccaattccaaagtggtggtgccaactcgcccgccctgtacctgctcgacg gcctgcgcgcgcaggacgacttcagcggctgggacatcaacaccccggcg ttcgagtggtacgaccagtcgggcctgtcggtggtcatgccggtgggtgg ccagtcaagcttctactccgactggtaccagcccgcctgcggcaaggccg gttgccagacttacaagtgggagaccttcctgaccagcgagctgccggg tggctgcaggccaacaggcacgtcaagcccaccggaagcgccgtcgtcgg tctttcgatggctgcttcttcggcgctgacgctggcgatctatcaccccc agcagttcgtctacgcggagcgatgtcgggcctgttggacccctcccag gcgatgggtcccaccctgatcggcctggcgatgggtgacgctggcggcta caaggcctccgacatgtggggcccgaaggaggacccggcgtggcagcgca acgacccgctgttgaacgtcgggaagctgatcgccaacaacacccgcgtc tgggtgtactgcggcaacggcaagccgtcggatctgggtggcaacaacct
```

-continued
gccggccaagttcctcgagggcttcgtgcggaccagcaacatcaagttcc aagacgcctacaacgccggtggcggccacaacggcgtgttcgacttcccg gacagcggtacgcacagctgggagtactggggcgcgcagctcaacgctat gaagcccgacctgcaacgggcactgggtgccacgcccaacaccgggcccg cgccccagggcgcctag SEQ ID NO: 3
(15 AMINO ACID AG85A TRUNCATION POLYPEPTIDE
SEQUENCE)
MQLVDRVRGAVTGMSRRLVVGAVGAALVSGLVGAVGGTATAGAFSRPGLP
VEYLQVPSPSMGRDIKVQFQSGGANSPALYLLDGLRAQDDFSGWDINTPA
FEWYDQSGLSVVMPVGGQSSFYSDWYQPACGKAGCQTYKWETFLTSELP
GWLQANRHVKPTGSAVVGLSMAASSALTLAIYHPQQFVYAGAMSGLLDPS
QAMGPTLIGLAMGDAGGYKASDMWGPKEDPAWQRNDPLLNVGKLIANNTR
VWVYCGNGKPSDLGGNNLPAKFLEGFVRTSNIKFQDAYNAGGGHNGVFDF
PDSGTHSWEYWGAQLNAMKPDLQR SEQ ID NO: 4
(15 AMINO ACID AG85A TRUNCATION NUCELOTIDE SEQUENCE)
atgcagcttgttgacagggttcgtggcgccgtcacgggtatgtcgcgtcg
actcgtggtcggggccgtcggcgcggccctagtgtcgggtctggtcggcg
ccgtcggtggcacggcgaccgcgggggcattttcccggccgggcttgccg
gtggagtacctgcaggtgccgtcgccgtcgatgggccgtgacatcaaggt
ccaattccaaagtggtggtgccaactcgcccgccctgtacctgctcgacg
gcctgcgcgcgcaggacgacttcagcggctgggacatcaacaccccggcg
ttcgagtggtacgaccagtcgggcctgtcggtggtcatgccggtgggtgg
ccagtcaagcttctactccgactggtaccagcccgcctgcggcaaggccg
gttgccagacttacaagtgggagaccttcctgaccagcgagctgccgggg
tggctgcaggccaacaggcacgtcaagcccaccggaagcgccgtcgtcgg
tctttcgatggctgcttcttcggcgctgacgctggcgatctatcaccccc
agcagttcgtctacgcgggagcgatgtcgggcctgttggacccctcccag
gcgatgggtcccaccctgatcggcctggcgatgggtgacgctggcggcta
caaggcctccgacatgtggggcccgaaggaggacccggcgtggcagcgca
acgacccgctgttgaacgtcgggaagctgatcgccaacaacacccgcgtc
tgggtgtactgcggcaacggcaagccgtcggatctgggtggcaacaacct
gccggccaagttcctcgagggcttcgtgcggaccagcaacatcaagttcc
aagacgcctacaacgccggtggcggccacaacggcgtgttcgacttcccg
gacagcggtacgcacagctgggagtactggggcgcgcagctcaacgctat
gaagcccgacctgcaacgg SEQ ID NO: 5
The 1176 nucleotide sequence of the insert is as follows (expressed sequence in upper case, Ag85A coding sequence underlined):
tctgtacgggcccgtacggtaccgagctcggatctgcgcgccgccaccAT
GGATGCAATGAAGAGAGGGCTCTGCTGTGTGCTGCTGCTGTGTGGAGCAG
TCTTCGTTTCGCCCAGCCAGGAAATCCATGCCCGATTCAGAAGAGGATCT -continued ATGCAGCTTGTTGACAGGGTTCGTGGCGCCGTCACGGGTATGTCGCGTCG
ACTCGTGGTCGGGGCCGTCGGCGCGGCCCTAGTGTCGGGTCTGGTCGGCG
CCGTCGGTGGCACGGCGACCGCGGGGGCATTTTCCCGGCCGGGCTTGCCG
GTGGAGTACCTGCAGGTGCCGTCGCCGTCGATGGGCCGTGACATCAAGGT
CCAATTCCAAAGTGGTGGTGCCAACTCGCCCGCCCTGTACCTGCTCGACG
GCCTGCGCGCGCAGGACGACTTCAGCGGCTGGGACATCAACACCCCGGCG
TTCGAGTGGTACGACCAGTCGGGCCTGTCGGTGGTCATGCCGGTGGGTGG
CCAGTCAAGCTTCTACTCCGACTGGTACCAGCCCGCCTGCGGCAAGGCCG
GTTGCCAGACTTACAAGTGGGAGACCTTCCTGACCAGCGAGCTGCCGGGG
TGGCTGCAGGCCAACAGGCACGTCAAGCCCACCGGAAGCGCCGTCGTCGG
TCTTTCGATGGCTGCTTCTTCGGCGCTGACGCTGGCGATCTATCACCCCC
AGCAGTTCGTCTACGCGGGAGCGATGTCGGGCCTGTTGGACCCCTCCCAG
GCGATGGGTCCCACCCTGATCGGCCTGGCGATGGGTGACGCTGGCGGCTA
CAAGGCCTCCGACATGTGGGGCCCGAAGGAGGACCCGGCGTGGCAGCGCA
ACGACCCGCTGTTGAACGTCGGGAAGCTGATCGCCAACAACACCCGCGTC
TGGGTGTACTGCGGCAACGGCAAGCTGTCGGATCTGGGTGGCAACAACCT
GCCGGCCAAGTTCCTCGAGGGCTTCGTGCGGACCAGCAACATCAAGTTCC
AAGACGCCTACAACGCCGGTGGCGGCCACAACGGCGTGTTCGACTTCCCG
GACAGCGGTACGCACAGCTGGGAGTACTGGGGCGCGCAGCTCAACGCTAT
GAAGCCCGACCTGCAACGTGGATCCATTCCAAACCCTTTGCTGGGATTGG
ACtgactgcagatatccatcacactg SEQ ID NO: 6
MDAMKRGLCCVLLLCGAVFVSPSQEIHARFRRGSMQLVDRVRGAVTGMSR
RLVVGAVGAALVSGLVGAVGGTATAGAFSRPGLPVEYLQVPSPSMGRDIK
VQFQSGGANSPALYLLDGLRAQDDFSGWDINTPAFEWYDQSGLSVVMPVG
GQSSFYSDWYQPACGKAGCQTYKWETFLTSELPGWLQANRHVKPTGSAVV
GLSMAASSALTLAIYHPQQFVYAGAMSGLLDPSQAMGPTLIGLAMGDAGG
YKASDMWGPKEDPAWQNDPLLNVGKLIANNTRVWVYCGNGKLSDLGGNNL
PAKFLEGFVRTSNIKFQDAYNAGGGHNGVFDFPDSGTHSWEYWGAQLNAM
KPDLQRGSIPNPLLGLD

The invention claimed is:

1. An immunogenic composition comprising a non-replicating or replication impaired poxvirus vector expressing the translation product of a mycobacterial Ag85a gene, wherein the poxvirus vector expresses Ag85a with a PK C-terminus tag, a TPA leader sequence and a truncated C-terminus.

2. The composition of claim 1, wherein the non-replicating or replication impaired poxvirus vector is Modified Vaccinia Ankara (MVA).

3. The composition of claim 1, wherein the poxvirus vector expresses the translation product of SEQ ID NO:5.

4. The composition of claim 1, wherein the poxvirus vector further expresses the translation product of at least one additional antigen gene(s) from a mycobacterial species.

5. The composition of claim 1, wherein the immunogenic composition further comprises at least one additional antigen and/or antimicrobial.

6. The composition of claim 1, wherein the immunogenic composition is capable of inducing a T cell response that is protective against a disease selected from the group consisting of tuberculosis, leprosy, *Mycobacterium avium* infection, non-tuberculosis mycobacterial infection, Buruli ulcer, *Mycobacterium Bovis* infection or disease, smallpox, monkeypox, *Mycobacterium paratuberculosis* infection, inflammatory bowel disease, Crohn's disease, autoimmune disease, cancer and bladder cancer.

7. A vectored vaccine comprising a non-replicating or replication impaired poxvirus vector expressing a polypeptide comprising the translation product of the nucleotide sequence of SEQ ID NO:4, a PK C-terminus tag and a TPA leader sequence.

8. The vectored vaccine of claim 7, wherein the polypeptide comprising the translation product of the nucleotide sequence of SEQ ID NO:4, a PK C-terminus tag and a TPA leader sequence is encoded by SEQ ID NO:5.

9. The vectored vaccine of claim 7, wherein the non-replicating or replication impaired poxvirus vector is MVA.

10. The vectored vaccine of claim 7, wherein the poxvirus vector further expresses a polypeptide comprising the translation product of an additional mycobacterial antigen gene.

* * * * *